United States Patent [19]
Graham

[11] Patent Number: 6,111,398
[45] Date of Patent: Aug. 29, 2000

[54] METHOD AND APPARATUS FOR SENSING AND CHARACTERIZING PARTICLES

[75] Inventor: Marshall Donnie Graham, Nicholasville, Ky.

[73] Assignee: Coulter International Corp., Miami, Fla.

[21] Appl. No.: 08/887,588

[22] Filed: Jul. 3, 1997

[51] Int. Cl.[7] .......................... G01N 15/12; G01N 27/07
[52] U.S. Cl. .......................................... 324/71.4; 73/61.71
[58] Field of Search ........................... 324/71.4; 73/61.71

[56] References Cited

U.S. PATENT DOCUMENTS

| | | |
|---|---|---|
| 2,656,508 | 10/1953 | Coulter . |
| 2,869,078 | 1/1959 | Coulter et al. . |
| 2,985,830 | 5/1961 | Coulter et al. . |
| 3,122,431 | 2/1964 | Coulter et al. . |
| 3,259,842 | 7/1966 | Coulter et al. . |
| 3,266,526 | 8/1966 | Berg . |
| 3,299,354 | 1/1967 | Hogg . |
| 3,361,965 | 1/1968 | Coulter et al. . |

(List continued on next page.)

OTHER PUBLICATIONS

Kachel, V., "Electrical Resistance Pulse Sizing: Coulter Sizing", *Flow Cytometry and Sorting*, Second Ed., pp. 45–80 (1990) (month unavailable).

*Primary Examiner*—Glenn W. Brown
*Attorney, Agent, or Firm*—Warren W. Kurz; Mitchell E. Alter

[57] ABSTRACT

Apparatus for sensing and characterizing particles (e.g., blood cells or ceramic powders) suspended in a liquid medium comprises a conduit through which the particle suspension is caused to pass simultaneously with an electrical current. According to the invention, the interior wall of the conduit effectively varies in resistivity along the length of the conduit to define a delimited central region of high electrical resistivity which is smoothly contiguous on its opposing boundaries to uninsulated distal elements of lesser electrical resistivity. The delimited central region of the conduit functions as a Coulter volumeter conduit. The uninsulated distal elements of the conduit are made to have a dimension along the conduit wall which is at least equal to the axial extent of the effective ambit electric fields of a traditional Coulter volumeter conduit having a cross-sectional geometry identical to that of the delimited central region of high resistivity in the improved volumeter conduit. According to a preferred embodiment of the invention, the delimited central region of the improved volumeter conduit is defined by a traditional Coulter conduit wafer, i.e., a dielectric wafer containing a central circular conduit, and the distal elements of lesser resistivity are defined by uninsulated, electrically conductive, circular collars attached to opposite sides of the conduit wafer. The conduit in the conduit wafer and the openings in the conductive collars collectively form a hydrodynamically smooth volumeter conduit, in which the electric and hydrodynamic fields of the traditional volumeter conduit are advantageously amended in the manner above noted.

65 Claims, 12 Drawing Sheets

U.S. PATENT DOCUMENTS

| | | |
|---|---|---|
| 3,502,973 | 3/1970 | Coulter et al. . |
| 3,502,974 | 3/1970 | Coulter et al. . |
| 3,628,140 | 12/1971 | Hogg et al. . |
| 3,638,677 | 2/1972 | Baccarini . |
| 3,668,531 | 6/1972 | Hogg . |
| 3,700,867 | 10/1972 | Hogg . |
| 3,701,029 | 10/1972 | Hogg . |
| 3,710,263 | 1/1973 | Doty et al. . |
| 3,710,264 | 1/1973 | Doty et al. . |
| 3,714,565 | 1/1973 | Coulter et al. . |
| 3,733,548 | 5/1973 | Coulter et al. . |
| 3,739,258 | 6/1973 | Karuhn et al. . |
| 3,739,268 | 6/1973 | Karuhn et al. . |
| 3,746,976 | 7/1973 | Hogg . |
| 3,771,058 | 11/1973 | Hogg . |
| 3,781,674 | 12/1973 | Claps . |
| 3,783,376 | 1/1974 | Doniguian . |
| 3,783,391 | 1/1974 | Hogg et al. . |
| 3,790,883 | 2/1974 | Bergegere . |
| 3,793,587 | 2/1974 | Thom et al. . |
| 3,810,010 | 5/1974 | Thom . |
| 3,863,159 | 1/1975 | Coulter et al. . |
| 3,863,160 | 1/1975 | Doty . |
| 3,871,770 | 3/1975 | von Behrens et al. . |
| 3,902,115 | 8/1975 | Hogg et al. . |
| 3,924,180 | 12/1975 | Salzman et al. . |
| 3,936,739 | 2/1976 | Hogg . |
| 3,940,691 | 2/1976 | Hogg . |
| 3,949,197 | 4/1976 | Bader . |
| 3,949,198 | 4/1976 | Coulter et al. . |
| 3,961,249 | 6/1976 | Coulter . |
| 3,979,669 | 9/1976 | Godin . |
| 3,987,391 | 10/1976 | Hogg . |
| 4,009,443 | 2/1977 | Coulter et al. . |
| 4,014,611 | 3/1977 | Simpson et al. . |
| 4,161,690 | 7/1979 | Feier . |
| 4,165,484 | 8/1979 | Haynes . |
| 4,253,058 | 2/1981 | Kachel et al. . |
| 4,290,011 | 9/1981 | Berg et al. . |
| 4,348,107 | 9/1982 | Leif . |
| 4,395,676 | 7/1983 | Hollinger et al. . |
| 4,434,398 | 2/1984 | Berg et al. . |
| 4,438,390 | 3/1984 | Hogg . |
| 4,484,134 | 11/1984 | Halloran . |
| 4,491,786 | 1/1985 | Godin . |
| 4,510,438 | 4/1985 | Auer . |
| 4,515,274 | 5/1985 | Hollinger et al. . |
| 4,525,666 | 6/1985 | Groves . |
| 4,673,288 | 6/1987 | Thomas et al. . |
| 4,710,021 | 12/1987 | von Behrens . |
| 4,760,328 | 7/1988 | Groves . |
| 4,797,624 | 1/1989 | Dunstan et al. . |
| 4,818,103 | 4/1989 | Thomas et al. . |
| 5,150,037 | 9/1992 | Kouzuki . |
| 5,402,062 | 3/1995 | Barnes et al. . |
| 5,432,992 | 7/1995 | Barnes et al. . |
| 5,623,200 | 4/1997 | Ogino . |

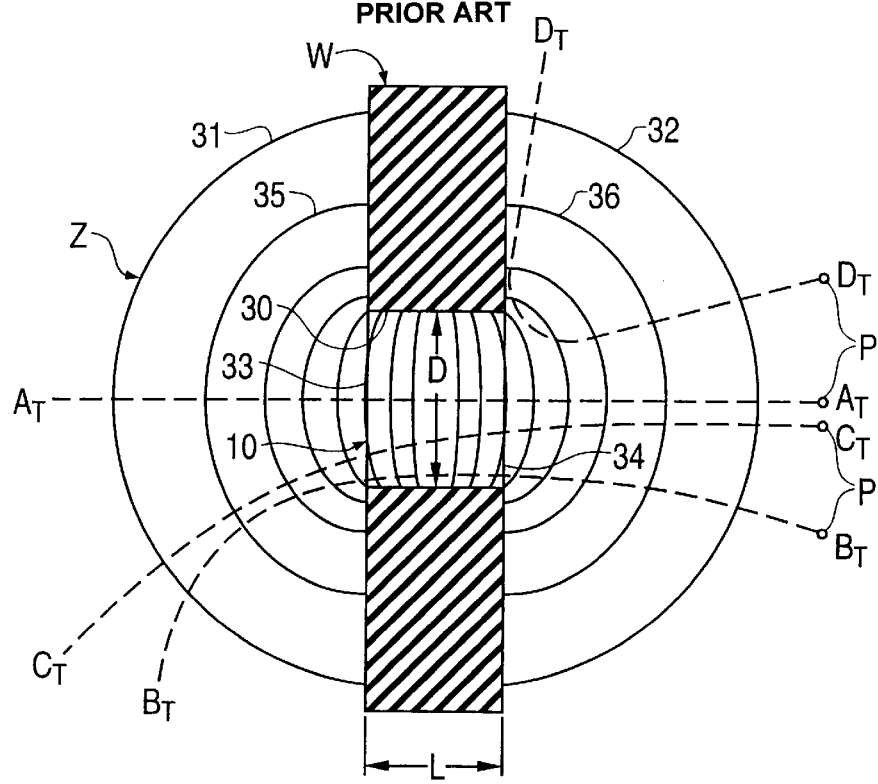
FIG. 2
PRIOR ART
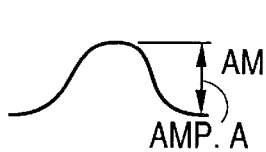
FIG. 4A
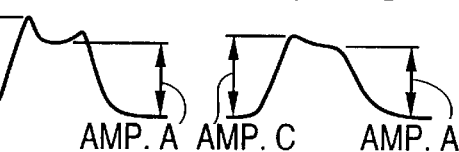
FIG. 4B FIG. 4C
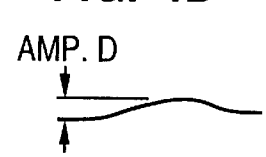
FIG. 4D

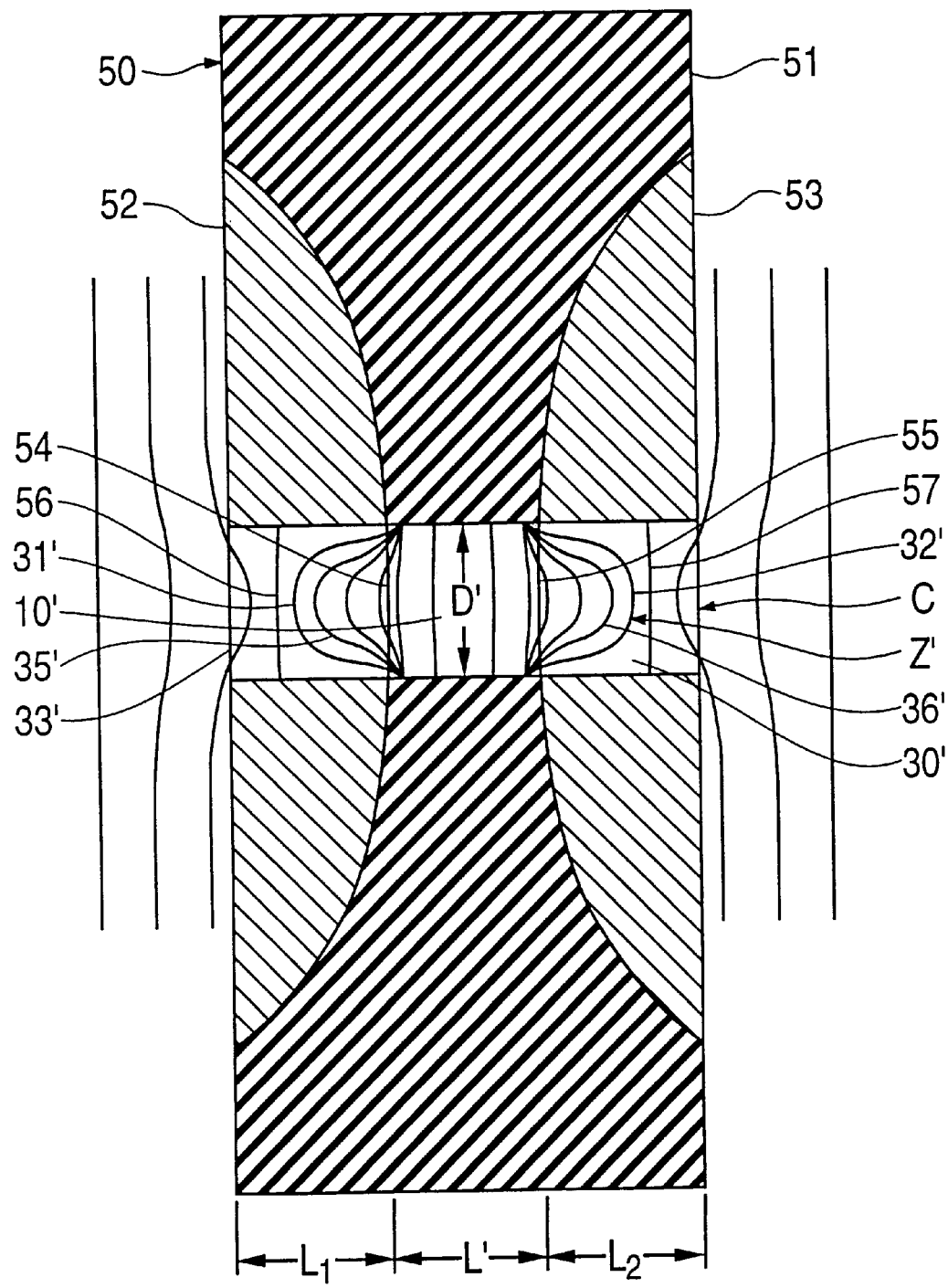

METHOD AND APPARATUS FOR SENSING AND CHARACTERIZING PARTICLES

BACKGROUND OF THE INVENTION

1. Field of the Invention

The present invention relates to improvements in methods and apparatus for sensing and characterizing small particles, such as blood cells or ceramic powders, suspended in a liquid medium having an electrical impedance per unit volume which differs from that of the particles. More particularly, it relates to improvements in methods and apparatus for sensing and characterizing such particles by the Coulter principle.

2. Discussion of the Prior Art

U.S. Pat. No. 2,656,508 to Wallace H. Coulter discloses a seminal method for sensing particles suspended in a liquid medium. An exemplary apparatus for implementing such method is schematically illustrated in FIG. 1. Such apparatus comprises a dual-compartment dielectric vessel 6 which defines first and second compartments 6A and 6B separated by a dielectric wall 7. Each of the compartments 6A and 6B is adapted to contain, and is filled with, a liquid medium M. The particles to be sensed and characterized are suspended at an appropriate concentration in liquid medium M and introduced into compartment 6A through a suitable inlet port 8 formed therein. Wall 7 is provided with a relatively large opening 7A which is sealed by a thin wafer W made of a homogeneous dielectric material. A small through-hole formed in wafer W provides a conduit 10, which constitutes the only operative connection between compartments 6A and 6B. An appropriate vacuum applied to an outlet port 11 suitably formed in compartment 6B causes the particle suspension to flow from compartment 6A to compartment 6B through conduit 10, discussed in detail below. Each particle in the suspension displaces its own volume of the particle-suspending liquid M, and conduit 10 provides a consistent reference volume against which that displaced volume may be compared. If the dimensions of conduit 10 and the concentration of particles in the suspension are appropriately selected, particles can be made to transit the conduit more or less individually. Conduit 10 thus functions as a miniature volumeter, capable under suitable conditions of making sensible the liquid displaced by individual microscopic particles.

To enable convenient sensing of the liquid displacement occasioned by particles transiting the conduit, the particle-suspending liquid M is made to have an electrical impedance per unit volume which differs from that of the particles. The contrast in electrical impedance between particle and suspending liquid thus converts the volume of displaced liquid into a proportional change in the electrical impedance of the liquid column filling conduit 10. Excitation electrodes 15 and 16 are respectively positioned in compartments 6A and 6B and electrically connected to a source 17 of electrical current, whereby a nominal electrical current is caused to flow through conduit 10 simultaneously with the particle suspension. Consequently, passage of a particle through conduit 10 produces a pulsation in the current flowing through the conduit which is proportional to the volume of liquid displaced by the particle. An AC-coupled sensing circuit 19, also electrically connected to excitation electrodes 15 and 16, operates to sense the pulsations in current between these electrodes. Thus, as individual particles pass through conduit 10, sensing circuit 19 produces an electrical signal pulse having an amplitude which is characteristic of the particle volume. Additional circuits 20 further process the particle signal pulses to provide a count of particles exceeding some particular volumetric threshold or, via the elegant positive-displacement metering system disclosed in U.S. Pat. No. 2,869,078 to Wallace H. Coulter and Joseph R. Coulter, Jr., the particle concentration. The volumetric distribution of the particles may be conveniently characterized by causing current source 17 to provide a constant current and analyzing the particle pulses with multiple-thresholding sizing circuitry 21 as described in U.S. Pat. No. 3,259,842 to Wallace H. Coulter et al. Alternatively, if current source 17 is caused to provide combinations of excitation currents, including at least one source of high-frequency alternating current as discussed in U.S. Pat. Nos. 3,502,973 and 3,502,974 to Wallace H. Coulter and W. R. Hogg, an apparent volume reflecting the internal composition of certain particles may be similarly characterized. Such characterization results are displayed or recorded by appropriate devices 22. This method of sensing and characterizing particles, by suspending them in a liquid medium having an electrical impedance per unit volume which differs from that of the particles and passing the resulting particle suspension through a constricting conduit while monitoring the electrical current flow through the conduit, has become known as the Coulter principle.

Central to the Coulter principle is the volumeter conduit 10 which enables electrical sensing of particle characteristics by constricting both the electric and hydrodynamic fields established in vessel 6. Although conduits of general longitudinal section and either circular or rectangular cross-sections are considered in the '508 patent, in this patent's practical example the conduit is a pinpoint circular aperture formed in the wall of a closed glass tube disposed within a second vessel so that both particle suspension and excitation current flow in the direction of the aperture axis between the two vessels. Such small apertures formed directly in a containment vessel are difficult to manufacture to repeatable geometry and tolerance. A practicable alternative utilized separate wafers cut from capillary tubing and sealed over a somewhat larger opening so that the tubing conduit formed the only operative connection between the two vessels; however, the conduit geometry in such wafers was unstable if sealing were done by the glass-fusion methods required for reliable seals. Ruby or sapphire jewels developed as anti-friction bearings for precision mechanical devices retain their geometry during fusion to glass, have excellent dielectric and mechanical properties, are readily available in a range of geometries and sizes, and so were indicated for use as conduit wafers in U.S. Pat. Nos. 2,985,830 and 3,122,431 to Wallace H. Coulter et al. The aperture tube described in these patents has been widely adapted, e.g., vessel 6 in FIG. 1, and ruby or sapphire ring jewels are frequently used as the conduit wafer W constricting the opening (e.g., 7A in wall 7) between containment compartments. As shown in the enlarged view of conduit wafer W in FIG. 2, a traditional Coulter volumeter conduit 10 thus comprises a continuous surface or wall 30 of length L which defines a right cylindrical opening of circular cross-section and diameter D through a homogeneous dielectric material of thickness L. Due to material homogeneity, the electrical resistivity of conduit wall 30 surrounding the flows of suspension and current through the conduit is substantially axisymmetric and uniform in any longitudinal conduit section. Because of its historical development, conduit wafer W is often called an "aperture wafer", and the traditional Coulter conduit 10 in conduit wafer W is commonly referred to as a "Coulter aperture".

The '508 patent describes two important functional properties as depending on the dimensions of Coulter volumeter conduits such as 10 in FIG. 1, viz., the volumetric sensitivity and the masking of one particle by another during simultaneous passage through the conduit volume. In principle, maximum volumetric sensitivity is obtained when the dimensions of volumeter conduit 10 approximate the diameter of the largest particle in the suspension of interest. Practically, conduit diameter D must approach twice the maximum particle diameter to minimize risk of clogging, and conduit length L is usually made as short as possible to minimize coincidence artifacts due to two or more particles simultaneously transiting the conduit. For a given conduit geometry, coincidence effects are only dependent on particle concentration and can be limited by increasing sample dilution. Industrial applications require various conduit diameters D between 0.010 mm and 2.000 mm, but many medical and scientific applications can be satisfied with conduit diameters D between 0.030 mm and 0.200 mm. Conduits with length-to-diameter ratio L/D=1.2 have been found to provide a combination of characteristics useful in a variety of applications, but medical applications benefit from the faster sample-throughput rates obtainable with less-diluted samples. As noted in the aforementioned U.S. Pat. No. 2,985,830, conduits with L/D=0.75 have proven a practicable compromise; such conduits permit acceptable processing rates and volumetric sizing of particles having diameters from about two percent, up to about 80 percent, of the conduit diameter D. In many applications decreased coincidence volumes or improved volumetric sensitivity would be advantageous, but field properties in the vicinity of the volumeter conduit frustrate use of shorter conduit lengths.

The '508 patent does not anticipate the complicating field properties of volumeter conduits such as 10 in FIG. 1. Since issuance of the '508 patent in 1953, the Coulter principle has been applied to a variety of particle-characterization problems important in numerous medical, scientific and industrial disciplines, and much experience has been gained with Coulter volumeter conduits. Many studies have been published regarding their functional properties, e.g., Volker Kachel, "Electrical Resistance Pulse Sizing: Coulter Sizing", to which reference is recommended for additional information (*FLOW CYTOMETRY AND SORTING*, 2nd. ed., M. R. Melamed, T. Lindmo, and M. L. Mendelsohn, eds., Wiley-Liss, New York, 1990, pages 45 to 80). Characteristics of signal pulses generated by particles passing through such conduits result from a complex interaction of the particles with both the electric field established in the liquid medium M by the current between excitation electrodes 15 and 16 and the hydrodynamic field established by the suspending liquid M carrying the particles through the conduit. Potential distributions for both fields show axisymmetric, semi-elliptical equipotentials at the entry orifice of the conduit, and for both fields, concentric flow converges toward this orifice. While the current through conduit 10 produces an electric field which is symmetric about the conduit midpoint as shown in FIG. 2, kinematic viscosity of the particle-suspending liquid causes a more complicated suspension flow through conduit 10 into compartment 6B. Some field properties of volumeter conduits relevant to the present invention may be summarized as follows:

1. As shown in the longitudinal section of conduit wafer W in FIG. 2, the particle-sensitive zone Z functionally includes not only the geometric volumeter conduit 10 defined by wall 30 but also the two semielliptical ambit electric fields 31 and 32 coaxial with, and outside the opposing ends of, the geometric conduit; the scale of these ambit fields depends only on the diameter D of the respective entrance and exit orifices, 33 and 34. In addition to producing current pulsations as they transit the geometric conduit, particles may also produce current pulsations if they pass through that portion of the suspending liquid M containing the ambit fields.

Consequently, the semielliptical equipotentials corresponding to the desired detectability threshold determine the effective spatial extent of the ambit fields 31 and 32. It can be shown that the portion of the particle-sensitive zone occupied by the geometric conduit 10 is (L/D)/(L/D+16K/3), where K is the product of the three diameter-normalized intercepts of the chosen threshold equipotential on a coordinate system with origins at the particular orifice center. It has been demonstrated that the effective ambit fields extend outward from the respective entrance and exit orifices 33 and 34 of volumeter conduit 10 approximately one conduit diameter D, with lateral intercepts at 1.15D, if pulse amplitudes from peripheral passages are to be limited to one percent of the theoretical maximum signal-pulse amplitude. For these one-percent equipotentials 35 and 36, the axial length of sensitive zone Z is (L+2D), K=1.3225, and for L/D=1.2 more than 85 percent of the particle-sensitive zone is external to the geometric Coulter conduit 10. The spatial extent of the sensitive zone increases the likelihood of particle coincidence, requiring greater sample dilution and processing times. In addition, the spatial extent of sensitive zone Z limits pulse signal-to-noise ratios, and therefore particle detectability, in two ways. First, particle contrasts and so pulse amplitudes are limited, since the volumetric sensitivity depends on the ratio of liquid volume displaced by each particle to the volume of liquid in the sensitive zone; and secondly, the noise tending to mask particle contrasts is increased, since it originates thermally throughout this latter volume. In principle, shorter conduit lengths L can decrease particle coincidence, increase conduit volumetric sensitivity, and decrease thermal noise; in practice, the benefits of decreasing conduit length are limited because, as L approaches zero, sensitive zone Z collapses to the ambit ellipsoid with volume determined by the conduit diameter and the desired threshold of pulse detectability.

2. The electric field forming that portion of particle-sensitive zone Z within the geometric volumeter conduit 10 is inhomogeneous, only approaching homogeneity at the conduit midpoint for L/D ratios of 2.0 or greater. Midpoint field inhomogeneity introduces errors of two types into particle pulses, viz., particles transiting the conduit along axial trajectories fail to generate fully-developed pulse amplitudes for conduits with L/D ratios less than 2.5, and particles with similar contrasts generate pulse amplitudes depending on the radial position of the particle trajectory, regardless of the L/D ratio of the conduit. Further, as will be discussed in Item 4, particles transiting the annular region containing the intense gradients at orifices 33 and 34 generate pulses having anomalous characteristics. This region, from conduit wall 30 inward to a radius r=0.75(D/2) for typical Coulter volumeter conduits, also defines the maximum particle diameter for which linear volumetric response is obtained.

3. Conduit hydrodynamics determine particle presentation to particle-sensitive zone Z and, therefore, characteristics of the pulse generated by a given particle as it transits the geometric volumeter conduit. In response to the driving pressure gradient, the particle suspension in the sample compartment (6A in FIG. 1) develops concentric laminar flow accelerating toward volumeter conduit 10. At the entry orifice 33 in FIG. 2, the velocity profile of the constricting flow is quasi-uniform and of a magnitude determined by the desired sample volume, the time allowed to process it, and the cross-sectional area of the conduit. The flow just inside the conduit includes a shear layer at conduit wall 30, and particularly for L/D ratios less than about 3.0, the flow profile depends on the edge sharpness of entry orifice 33 and on how closely the kinematic viscosity of the suspending liquid permits it to follow the orifice geometry. When curvature of the edge at orifice 33 is sufficiently gradual, viscosity causes a transition from a quasi-uniform velocity profile toward the parabolic velocity profile of laminar flow (for practical reasons, orifice edges are usually sharp, and the shear layer surrounding the developing laminar flow may thicken to appreciably constrict the apparent flow cross-section). As is known in the fluidic art, for a circular conduit having a given L/D ratio, the degree of laminarity $\xi$ in a developing profile is inversely proportional to the Reynold's number $\Re e$, i.e., $\xi$ x/(R $\Re e$), where x is the distance into the conduit from the entry orifice and R=D/2. Standard fluidic methods permit calculation of the differential volumetric flowrates through given annular cross-sections of conduit 10 centered on any particular radius. The results of such calculations for a typical suspending liquid M are shown in FIG. 3 for conduits with L/D=0 (a), 0.75 (b), 1.20 (c), 3.60 (d) and $\infty$ (e); here, (e) illustrates fully developed laminar flow in an infinitely long conduit. Although conduits with L/D ratios of 3.6 provide significant laminarity (d), flow through the conduit approaches (e) only for L/D ratios significantly greater than 10. The most-frequent, or modal, particle trajectories occur at the radius r corresponding to the maximum value (dotted) of these differential volumetric flow characteristics. At entry orifice 33, L/D=0 as in (a), and the modal particle trajectory thus occurs at r=(D−p)/2, or typically within a particle diameter p of conduit wall 30. For small particles, the entrance modal trajectory thus coincides with the outer shear layer of the quasi-uniform flow profile. Regardless of the sharpness of the edge of the entry orifice 33, flow at the exit orifice 34 is jetting flow (into the receiving compartment 6B in FIG. 1), with a toroidal low-pressure region surrounding the jet and overlapping the exit ambit field 32. As shown in FIG. 3, for particles exiting orifice 34 in FIG. 2, the modal trajectories occur in annuli centered at radii r=0.82(D/2) or 0.76(D/2) for conduits with L/D=0.75 (b) or 1.20 (c), respectively, and significant numbers of particles transit the conduit outside r=0.75(D/2), through the orifice gradients of the sensitive zone. The combination of a sharp edge at orifice 33 and the low L/D ratios of typical volumeter conduits also minimizes the stabilizing effect of viscosity, and as a consequence, both the through-flow and jetting patterns are sensitive to imperfections in the edge of entry orifice 33. Conduit L/D ratios of 2.0 or greater result in both smoother flow through the geometric volumeter conduit and less turbulence in the jetting zone outside the exit orifice; exit modal trajectories for such conduits are centered inside r=0.725(D/2).

4. In volumetric applications of Coulter volumeter conduits, the most significant hydrodynamic effects are those on particle trajectory, shape, and orientation during passage through the particle-sensitive zone. As has been noted, the sensitive zone Z extends outward about one conduit diameter D from the entry orifice 33 in FIG. 2 and is overlapped by the convergent flow into conduit 10. Particles P in the sample vessel are entrained in the constricting flow and accelerated toward the entry orifice 33. As they enter the entry ambit 31 of the sensitive zone, particles on near-axial trajectories (e.g., trajectory $A_T$) may be deformed by the pressure field, and nonspherical particles will be oriented with their long dimension parallel to flow; such particles generate pulses similar to the pulse of FIG. 4A. Particles entering the sensitive zone outside an axial cone approximately 50 degrees in half-angle will, in addition, be accelerated around the edge at orifice 33 and through the conduit in the annulus near wall 30 containing the intense orifice gradients. These orifice gradients cause particles on trajectories such as $B_T$ in FIG. 2 to generate M-shaped pulses (e.g., pulse of FIG. 4B) of anomalous amplitude (e.g., amplitude B) and duration due to gradients in, respectively, conduit field and liquid flow. Particles on an intermediate trajectory (e.g., $C_T$ in FIG. 2) may generate asymmetric pulses, such as the pulse in FIG. 4C, which demonstrate anomalous amplitude (e.g., amplitude C) only on their leading edge. The frequency of such pulses depends on the portion of the conduit cross section occupied by the orifice gradients and the average radial position of the modal trajectories, which in turn is determined by the length L of the conduit. Moreover, decelerating particles that have exited the geometric volumeter conduit 10 may be drawn back into the exit ambit 32 (e.g., trajectory $D_T$ in FIG. 2) as the suspending liquid recirculates into the toroidal low-pressure region surrounding the exit jet; if so, they generate extraneous pulses of low amplitude and long duration as shown by the pulse of FIG. 4D. Both recirculation and wall trajectories have adverse consequences significant in many applications of the Coulter principle, as illustrated in FIG. 5. In contrast to an ideal volumetric distribution 40, the recirculating particles (e.g., trajectory $D_T$ in FIG. 2) result in a secondary distribution 41 in the actual sample distribution 43; this spurious distribution reduces dynamic volumetric range and, for polydisperse samples, may altogether preclude analysis of the smaller particles. Due to their anomalous pulse amplitudes, particles following wall trajectories (e.g., $B_T$ and $C_T$ in FIG. 2) introduce artifactual high-volume skewness 42 into the actual sample distribution 43, so degrading system ability to resolve particles of nearly identical volumes. Conduits with L/D=3.3 have been shown to reduce skewness inaccuracies; then, exit modal trajectories are centered inside r=0.66 (D/2).

Initially, apparatus based on the Coulter principle proved so extremely useful that data inaccuracies due to these functional conduit properties were tolerated. Gradually, however, data artifacts have become unacceptable impediments, particularly in applications where highly automated implementations are desirable, and so have prompted a broad variety of prior-art techniques intended to improve the accuracy of Coulter apparatus. This facilitating art will be summarized, for two purposes: Firstly, to illustrate the real difficulty in acceptably automating the Coulter principle, and secondly, to emphasize the advantages of the present invention. Such facilitating techniques include ones involving only the volumeter conduit, ones integrating the conduit into a subassembly, or those applying post-collection processing methods to the particle data. Some of this facilitating art has led to a requirement for one or more of the following in FIG. 1: a flow director 9, a second inlet port 12, and additional signal processing circuits 23, 24, and 25, each of which will be discussed in connection with the relevant art.

As noted in Item 1) above, the spatial extent of sensitive zone Z in FIG. 2 defines the coincidence, sensitivity, and noise characteristics of a given Coulter volumeter conduit. Because the diameter D of conduit 10 is usually determined by clogging concerns and its minimum length L as a compromise between artifacts due to coincidence and field inhomogeneities, variations in conduit geometry have been investigated as a means of improving functional properties. In the '508 patent, longitudinal conduit profiles other than right circular cylinders were disclosed as a means of varying the electric field along the geometric conduit and so establishing a desired particle pulse-shape. Ring jewels with various longitudinal bore profiles are available and so have seen application as conduit wafers, typically to facilitate mechanical goals. One early example used a straight ring jewel with a single spherical cup at the exit (U.S. Pat. No. 3,266,526); other examples use similar jewels but with the spherical cup at the conduit entry (U.S. Pat. Nos. 3,638,677; 3,783,376; 4,710,021; 5,150,037; 5,402,062; and 5,432,992). Such jewels retain sharp orifices due to the large radius of their spherical cups and so are functionally indistinguishable from the art first taught in U.S. Pat. No. 2,985,830. Functional improvement may be gained through a better fluidic match between the concentric entry flow and the quasi-uniform flow inside the entry orifice. Conduits which achieve this by mechanically limiting the off-axial extent of both the electric and fluidic fields at one or both orifices are described in U.S. Pat. No. 3,628,140 to W. R. Hogg and Wallace H. Coulter. Here, a jetting nozzle including a conical cup with half-angle of about 45 degrees is used to couple one or both conduit orifices to the adjacent volume of liquid. Although the patent attributes the resulting volumetric improvement to focusing of the excitation current, a more probable explanation lies in the observation, noted in Item 4) above, that particles entering the conduit within an axial cone of half-angle less than 50 degrees avoid the most intense artifactual effects of both conduit fields. The concept of the conical profile has also been adapted to conduits for use with optical sensing modalities, e.g., square or circular cross sections are described in U.S. Pat. No. 4,348,107 to R. C. Leif or U.S. Pat. No. 4,515,274 to J. D. Hollinger and R. I. Pedroso, respectively. Such conduits of square and triangular cross section, and techniques for constructing them by assembling multiple truncated dielectric pyramids, have been described (U.S. Pat. Nos. 4,673,288 and 4,818,103). Mechanical restriction of the conduit fields also decreases the volume occupied by the conduit ambits, with attendant improvement in the coincidence, noise, and recirculation characteristics of the conduit; an extreme form of this approach (U.S. Pat. No. 4,484,134 to M. T. Halloran) is discussed below. In U.S. Pat. No. 5,623,200, longitudinal profiles are described as a method of reducing magnitudes of the orifice gradients. Typically, however, pulse rise-times suffer due to the gradual change in cross section, and acceptable pulse characteristics usually require that the tapered section(s) be blended into a spherical cup centered on the conduit orifice, as is also taught in U.S. Pat. No. 3,628,140. In U.S. Pat. No. 3,733,548 to Wallace H. Coulter and W. R. Hogg, a semicircular longitudinal profile is described as producing better electric-field uniformity than the original Coulter conduit and, in principle, should also offer significant inlet flow matching. Yet another design (U.S. Pat. No. 3,739,258) primarily addresses flow matching, through use of a trumpet-shaped inlet to reduce thickening of the entry shear layer. Neither of the latter conduits significantly improves limitations due to the conduit ambit fields, and without further augmentation none of the above-discussed profiles yield data sufficiently artifact-free to be of wide use. In typical wafer dielectrics, all such shaped conduits are difficult to manufacture to practicable precision, and so all are expensive to produce. In some applications they may worsen the clogging problem.

Particle coincidence degrades count data directly through lost particle pulses. It also degrades volumetric data indirectly through inappropriate inclusion of misshapen pulses in the volumetric distribution. In some applications, adaptive dilution may acceptably limit coincidence artifact (U.S. Pat. No. 3,979,669 to T. J. Godin), or adaptive extension of the counting period may acceptably compensate it (U.S. Pat. No. 4,009,443 to Wallace H. Coulter et al.); but the resulting variable processing times are undesirable in many applications. In principle, the pulse loss due to coincidence can be predicted statistically, and many post-collection corrective techniques, e.g., coincidence-correction circuit 23 in FIG. 1, have been described in the scientific and patent literature; see, e.g., U.S. Pat. No. 3,949,197 to H. Bader for a review and example.

Other approaches estimate pulse loss based on pulse occurrence rate, count, or duration, e.g., U.S. Pat. No. 3,790,883 to P. Bergegere; U.S. Pat. No. 3,936,739 and U.S. Pat. No. 3,940,691 to W. R. Hogg; U.S. Pat. No. 3,949,198 to Wallace H. Coulter and W. R. Hogg; and U.S. Pat. No. 3,987,391 to W. R. Hogg. Limitations of several are discussed in U.S. Pat. No. 4,510,438 to R. Auer, which proposes correction for the actual coincidence rate as determined by an independent optical sensing modality. These methods may acceptably correct count data for coincidence pulse loss when automated for specific applications, but only those which inhibit incorporation of misshapen pulses can improve the population volumetric distribution. All add to design complexity, and some require extensive computational resources.

The volumetric sensitivity and noise characteristics of Coulter volumeter conduits limit dynamic measurement range, particularly for smaller particles. Noise originates by two mechanisms, heating noise resulting from dissipation of the excitation current in the resistance of the particle-sensitive zone, and Johnson noise generated in this resistance. These limit the maximum practicable excitation current, on the one hand, and fundamental particle detectability on the other. In the prior art, heating noise has been reduced by providing thermally conductive paths leading away from conduit 10. U.S. Pat. No. 3,361,965 to Wallace H. Coulter and Joseph R. Coulter, Jr., describes one such structure, in which one electrode is formed as a plated metallic coating on the outer surface of the aperture tube. In U.S. Pat. No. 3,714,565 to Wallace H. Coulter and W. R. Hogg the electrical path length through the suspending liquid, and so the thermal noise, is reduced by replacing the second electrode with a metallic element either composing, or coated onto the inner surface of, the aperture tube wall. The thermal effects are described more fully in U.S. Pat. No. 3,771,058 to W. R. Hogg; here, volumeter conduit 10 is formed in a wafer of thermally conductive dielectric and thermally connected to remote cooler regions via electrically and thermally conductive metallic coatings extending onto both planar surfaces of the conduit wafer. In U.S. Pat. No. 4,760,328 the same geometry is described in a structure which integrates sensing electronics onto the sapphire wafer. In all four of these patents the conductors cover extensive areas of the structure and variously approach volumeter conduit 10, but do not extend so close to the conduit as to interact with the effective ambit fields of its particle-sensitive zone Z. However, in U.S. Pat. No. 3,924,180 the Coulter conduit structure is modified by incorporation of thin conductors into the conduit structure, contiguous to conduit orifices 33 and 34, so forming potential-sensing electrodes in a dielectric sandwich through which the conduit penetrates; the intent is to minimize noise contributions to the sensed particle signal from the liquid outside the conduit ambits 31 and 32. Other techniques attempt to minimize noise effects, as for example the noise discriminator described in U.S. Pat. No. 3,781,674 to W. A. Claps, or the averaging of signals from tandem conduit/electrode structures similar to those of U.S. Pat. No. 3,924,180 to reduce Johnson noise as described in U.S. Pat. No. 4,438,390 to W. R. Hogg. In critical applications, certain of these may reduce heating noise generated in the conduit, but none significantly improves the volumetric sensitivity. U.S. Pat. Nos. 3,924,180 and 4,438,390 are the subject of further discussion, to follow.

As noted in Item 4) above, the effective sensitivity of Coulter volumeter conduit 10 may be further limited by the effects of exiting conduit flow carrying particles back into exit ambit field 32 of sensitive zone Z, e.g., trajectory $D_T$ in FIG. 2. These decelerating particles pass through the intense orifice field gradients and in many polydisperse samples result in long pulses of amplitudes comparable to those produced by the smaller particles. Unless precautions are taken to reduce the effects of these recirculating particles, both conduit sensitivity and usable dynamic range are degraded. In addition, when pulse-height techniques are used to develop volumetric distributions the pulses from recirculating particles cause extraneous peaks and broadening of actual particle distributions. At cost of reduced sample throughput, recirculation pulses may be excluded by pulse gating, e.g., by recursor pulse-edit circuit 24 in FIG. 1, either through analysis of pulses from the standard conduit or in response to a thin auxiliary detection electrode located in the conduit's geometric cylinder (U.S. Pat. No. 4,161,690). Longitudinal conduit profiles can mechanically reduce the liquid volume available to such particles and may be beneficial in some applications, as noted in the aforementioned U.S. Pat. No. 3,628,140 to W. R. Hogg and Wallace H. Coulter. Other applications are more critical, and many subassemblies incorporating the volumeter conduit have been described which attempt to prevent particles from recirculating into the conduit ambit fields. These either structure the exit flow path so that particles are mechanically prevented from re-entering the sensitive zone (U.S. Pat. Nos. 3,299,354 and 3,746,976 to W. R. Hogg or U.S. Pat. No. 4,484,134 to M. T. Halloran), use auxiliary fluidic circuits to dynamically sweep exiting particles away from the exit orifice (U.S. Pat. No. 4,014,611 to R. O. Simpson and T. J. Godin) or combine these two approaches (U.S. Pat. No. 3,902,115 to W. R. Hogg et al. and U.S. Pat. No. 4,491,786 to T. J. Godin, which contains a review of such methods). Other implementations have also been described (U.S. Pat. Nos. 4,253,058; 4,290,011; 4,434,398; 4,710,021; 5,402,062; 5,432,992; and 5,623,200). The dynamic sweep-flow method is widely used and involves metering appropriate volumes of the liquid medium M through a second inlet port 12 in FIG. 1, whereby the particles exiting conduit 10 are swept out of exit ambit field 32. These complex subassemblies can essentially eliminate recirculating particles, may include shaped conduits, and often include additional structure addressing effects of particles following wall trajectories. However, the large fluid volumes required for effective sweep-flow make it impractical to volumetrically determine particle concentration by positive-displacement methods. The approach taken by M. T. Halloran (in the aforementioned U.S. Pat. No. 4,484,134) potentially avoids need for auxiliary fluidic circuits and structures, by extending the insulating discs of U.S. Pat. No. 3,924,180 into an elongate tubular configuration; of an inner diameter substantially equal to that of the volumeter conduit, such extensions mechanically prevent recirculation of exiting particles into the exit ambit of the conduit and when carefully constructed can provide fluidic advantages of long conduits. However, for many applications of the Coulter principle such structures require complex mechanical designs difficult to construct to the necessary precision and tend to clog in use, due to their fluidic length.

The effective resolving ability of Coulter volumeter conduit 10 is determined by the hydrodynamic effects discussed in Item 4) above, specifically those carrying particles through the geometric conduit near its wall 30. The resultant characteristic M-shaped pulses (e.g., those in FIG. 4B or 4C) produce artifacts in the volumetric distribution, the importance of which is attested by the large amount of remedial prior art addressing them. This art is divided between two approaches, the early post-collection one of excluding the M-shaped pulses from the processed data and the later direct one of hydrodynamically controlling presentation of particles to the sensitive zone of the conduit. The electric field in the conduit sensitive zone Z, and particle trajectories (e.g., BT or CT) through it which produce problematic pulses, are illustrated in FIG. 2. Deletion of such pulses from the volumetric distribution data is suggested in U.S. Pat. No. 3,668,531 to W. R. Hogg, from which FIG. 2 is adapted. Other approaches have been described (U.S. Pat. Nos. 3,700,867 and 3,701,029 to W. R. Hogg; U.S. Pat. Nos. 3,710,263 and 3,710,264 to E. N. Doty and W. R. Hogg; U.S. Pat. No. 3,783,391 to W. R. Hogg and Wallace H. Coulter; U.S. Pat. No. 3,863,160 to E. N. Doty; and U.S. Pat. No. 3,961,249 to Wallace H. Coulter), all of which incorporate gating circuitry (25 in FIG. 1) responsive to various anomalous parameters of the misshapen pulses by which these pulses may be deleted from the pulse train processed for population distributions. Some of these are discussed in U.S. Pat. No. 3,863,159 to Wallace H. Coulter and E. N. Doty and in U.S. Pat. No. 4,797,624 to H. J. Dunstan et al., either of which well illustrates such gating methods. Gating may also be done in response to a detection signal from an auxiliary electrode (U.S. Pat. No. 4,161,690). The complexity of working implementations encouraged other approaches, and a simple flow-aligning device in front of the Coulter conduit was shown to improve volumetric accuracy (U.S. Pat. Nos. 3,739,268; 4,290,011; and 4,434,398). Further improvement was gained by injecting the particle stream directly into the conduit through an auxiliary flow director (U.S. Pat. No. 3,793,587 to R. Thom and J. Schulz and U.S. Pat. No. 3,810,010 to R. Thom), a technique now known as hydrodynamically focused flow. If in FIG. 1 the particle suspension is introduced through flow director 9 while liquid medium M is appropriately metered through port 8, the particles entering compartment 6A will be entrained into a sheath of the liquid medium M and carried through conduit 10 in the core of the composite flow pattern, with two important consequences. Firstly, the directed flow pattern prevents particles entering conduit 10 on trajectories such as $B_T$ and $C_T$ in FIG. 2, thereby eliminating pulses such as those in FIGS. 4B and 4C. Secondly, all particles transit conduit 10 inside the sheath liquid, which serves to center the particle trajectories inside the cross section of conduit 10 having relatively homogeneous electric fields, further reducing occurrence of anomalous particle pulses such as the pulse of FIG. 4B. Numerous conduit subassemblies incorporating focused flow have been described (e.g., U.S. Pat. No. 4,014,611 to R. O. Simpson and T. J. Godin; U.S. Pat.

No. 4,395,676 to J. D. Hollinger and W. R. Hogg; U.S. Pat. No. 4,484,134 to M. T. Halloran; U.S. Pat. No. 4,515,274 to J. D. Hollinger and R. I. Pedroso; and U.S. Pat. No. 4,525,666 to M. R. Groves; U.S. Pat. Nos. 3,871,770; 4,165,484; 4,253,058; 4,760,328; 5,150,037; and 5,623,200), some of which also include provisions addressing recirculating particles and the best of which can yield nearly ideal volumetric distributions. All add complexity to practical apparatus, and the large fluid volumes required for effective sample focusing make it impractical to volumetrically determine particle concentration by positive-displacement methods. Because the entraining sheath flow restricts the sample stream to a small central portion of the geometric volumeter conduit, a functional concentration of particles within this volume occurs and limitation of coincidence effects typically requires use of lower particle concentrations than with unfocused systems.

Nearly all of the prior art concerns traditional volumeter conduits and the two-terminal implementation of the Coulter principle described in the '508 patent, but this simple form has been elaborated in, e.g., U.S. Pat. Nos. 3,924,180; 4,438,390 to W. R. Hogg; and U.S. Pat. No. 4,484,134 to M. T. Halloran. The fluidic advantages of long conduits (i.e., ones having $L/D \geq 2$) have long been known, but the large coincidence volumes and noise levels associated with such conduits limit their practical usefulness. As has been discussed, in U.S. Pat. No. 3,924,180 thin insulated electrodes are located along the volumeter conduit to enable four-terminal potential sensing of particle pulsations from a small portion of the actual conduit length as one way of minimizing these limitations, and in U.S. Pat. No. 4,438,390 the structure of U.S. Pat. No. 3,924,180 is replicated in a single structure to produce a plurality of potential-sensitive zones in tandem, the potentials sensed thereby being averaged as a means of reducing Johnson noise. In U.S. Pat. No. 4,484,134 the insulative structures covering the electrodes in U.S. Pat. No. 3,924,180 are extended into tubular form, as has also been discussed. The plural electrodes incorporated into the conduit structures of these three patents are required to be as thin as practicable, to avoid significant influence on the conventional electric fields resulting from the excitation current, and are electrically connected to external sensing apparatus. The liquid column in these structures thus forms a resistance divider across which the total particle pulse amplitude is developed, but across only that section separating the potential-sensing electrodes of which is the sensed particle signal developed. Consequently, the loss of signal pulse amplitude due to the voltage-dividing action of the liquid column may offset any decrease in noise. Although these patents allude to fluidic advantages of the longer conduit structures, neither they nor the other known prior art either detail the origin of such advantages or suggest a specific method whereby such advantages may be systematically obtained.

There is no question that the accuracy, resolution, and convenience of Coulter apparatus have substantially benefited through the teachings of the many patents cited above, and fully automated apparatus is now available in which functional properties of the Coulter volumeter conduit are acceptably compensated. The Coulter principle has gained worldwide acceptance, and many national standards include methods based on it. Apparatus incorporating the Coulter principle is now available from a number of manufacturers, and its economic importance is attested by the voluminous prior art which has developed around it. However, much of this art concerns methods which increase apparatus complexity, with attendant decreased reliability and increased costs throughout the design, production, and maintenance cycle. Most requires multiple precision components difficult of manufacture and assembly to the requisite accuracy. Ones requiring auxiliary fluidic subsystems preclude positive-displacement volumetric determinations of particle concentration. Ones based on post-collection data processing discard particle data, and so require greater sample volumes or longer sample processing times. Each only mitigates an undesirable consequence of particle/field interaction in the particle-sensitive zone of the Coulter volumeter conduit, rather than amending the underlying characteristics of the electric and hydrodynamic fields. Because the prior art addresses their consequences, rather than their origins, functional properties of Coulter volumeter conduits have evolved little since the issuance of the '508 patent in 1953.

Reliability and cost competitiveness have become increasingly important considerations in apparatus design, and it would be advantageous to achieve the performance now attainable through the prior art summarized above, but without the increased complexity and costs associated with this art. It would be preferable to obviate such facilitating methods and apparatus, by directly amending field characteristics of the volumeter conduit. It would be desirable that any solution to this long-standing need be directly substitutable for the Coulter volumeter conduit of existing methods and apparatus, e.g., those of U.S. Pat. Nos. 2,656,508 or 3,259,842. It would also be desirable that this solution permit volumetric determination of particle concentration by positive-displacement methods such as, e.g., those described in U.S. Pat. No. 2,869,078.

SUMMARY OF THE INVENTION

In view of the foregoing discussion, an important object of this invention is to provide an improved apparatus of the type discussed above for sensing and characterizing particles, said apparatus combining accuracy in results with simplicity in construction.

Another object of the invention is to provide a volumeter assembly which, owing to its unique structure, operates to amend characteristics of the electric and hydrodynamic fields associated with the Coulter volumeter conduit, thereby simplifying the make-up of instruments of the type which sense and characterize particles by means of the Coulter principle.

Yet another object of this invention is to provide an improved method for sensing and characterizing particles by the Coulter principle.

In accordance with the present invention there is provided a new and improved apparatus for sensing and characterizing particles by the Coulter principle. As in the prior art, the apparatus of the invention comprises: (a) a volumeter conduit through which a liquid suspension of particles to be sensed and characterized can be made to pass, (b) a liquid handling-system for causing the particle suspension to pass through the volumeter conduit; (c) a first electrical circuit for producing a nominal electrical excitation current through the volumeter conduit, such excitation current being effective to establish in the vicinity of the volumeter conduit an electric field having a particle-sensitive zone in which changes in the nominal excitation current as produced by particles passing through the conduit simultaneously with the excitation current are measurable; and (d) a second electrical circuit for monitoring the amplitude of the electrical current through the volumeter conduit to sense the characteristics of particles passing through said conduit. In contrast to the prior-art apparatus, in which the volumeter conduit is formed in a homogeneous dielectric material so that the wall defining the conduit is of uniformly high electrical resistivity, the volumeter assembly in the new apparatus is so constructed that, in the broadest sense, the electrical resistivity of the wall defining the volumeter conduit therein is made to effectively vary in an axisymmetric manner along the conduit length (i.e., in a direction parallel to the flow of suspension through the conduit) so as to define a conduit having in any longitudinal conduit section a delimited central region of high electrical resistivity which is smoothly contiguous on its opposing boundaries to uninsulated distal regions of substantially lesser electrical resistivity. The electrical resistivity of the delimited central region is substantially greater, and the electrical resistivity of the uninsulated distal regions less, than that of the liquid in which the particles to be characterized are suspended. The delimited central high-resistivity region of the improved volumeter conduit functions as a traditional Coulter volumeter conduit. The uninsulated distal elements of the new volumeter conduit are made to have a minimum dimension along the conduit wall depending upon the desired detectability threshold in particle size, i.e., this dimension is made at least equal to the axial extent of the effective ambit electric fields of a traditional Coulter volumeter conduit having a cross-sectional geometry identical to that of the delimited central region of high resistivity in the improved volumeter conduit. Through their immersion in the suspending liquid, the uninsulated distal elements of the new volumeter conduit are electrically coupled to the electric field established by the excitation current through the high-resistivity region of the conduit. The uninsulated distal regions of the improved volumeter conduit assume independent potentials and independently function to amend both the electric and hydrodynamic fields in the vicinity of the volumeter conduit by: (i) shaping the electric field resulting from the excitation current so as to substantially confine the particle-sensitive zone within the physical boundaries of the conduit; (ii) enabling development of quasi-laminar flow through the particle-sensitive zone so as to significantly increase the proportion of particles per second transiting the substantially homogeneous areas of the particle-sensitive zone; and (iii) preventing particles that have already passed through the conduit and are on recirculating trajectories from re-entering the particle-sensitive zone.

The field-amending volumeter conduit of the invention affords the following advantages, when compared with prior-art volumeter conduits for sensing and characterizing particles:

1. The ambit electric fields of the particle-sensitive zone resulting from the excitation current are substantially smaller, thereby reducing the likelihood of particle coincidence while increasing volumetric sensitivity;
2. The cross section of the particle-sensitive zone containing substantially homogeneous field regions is significantly increased, thereby reducing the frequency of anomalous pulses and increasing the range in particle diameter for which the dynamic response is linear;
3. The suspension flow profile through the particle-sensitive zone is quasi-laminar rather than quasi-uniform, whereby the proportion of particles per second transiting the substantially homogeneous areas of the particle-sensitive zone is increased, further reducing the frequency of anomalous pulses; and
4. Particles are prevented from transiting the particle-sensitive zone on trajectories curving through the ambit electric fields, thereby eliminating both anomalous pulses due to particles entering the sensitive zone on high-angle trajectories and extraneous pulses due to exiting particles recirculating into the exit ambit field.

Because of these advantageous functional properties of the field-amending volumeter conduit, with Coulter apparatus incorporating it need is avoided for the complex assemblies and subsystems required by facilitating methods involving hydrodynamically-focused flow or sweep flow. Consequently, when compared with present apparatus for sensing and characterizing particles by the Coulter principle, apparatus incorporating the field-amending volumeter conduit of the invention affords some or all of the following further advantages:

A. Facilitating subsystems related to features 9, 12, 23, 24, and 25 in FIG. 1 may be eliminated, with significant reduction in manufacturing costs and appreciable improvement in system reliability but without important data inaccuracies;
B. Because no auxiliary fluidic subsystems are required, particle concentration may be readily determined by positive-displacement volumetric methods;
C. Because functional sample dilution due to sheath fluid is eliminated and need for post-collection pulse deletions can be significantly reduced, sample volumes and processing times may be reduced; and
D. Because of the significantly reduced coincidence volume compared to the Coulter volumeter conduit, the rate of sample throughput can be increased for a given detectability threshold and level of coincidence artifact, or a larger conduit diameter may be used to decrease clogging concerns.

According to another aspect of the invention, volumeter assemblies incorporating field-amending volumeter conduits may be embodied in a variety of dissimilar constructions. In one preferred embodiment, the field-amending volumeter conduit is defined by a through-hole formed in a disc of electrically inhomogeneous material. At the site selected for forming the through-hole, the electrical resistivity of the disc is made to effectively vary through the thickness thereof, e.g., by suitable doping, to define a central delimited region of high electrical resistivity which is contiguously bounded by uninsulated distal elements of substantially lesser electrical resistivity which intersect the faces of the disc. A hydrodynamically smooth opening of the desired cross-sectional and longitudinal geometry is then formed through the disc. The delimited central high-resistivity region of the volumeter conduit so formed functions as a traditional Coulter volumeter conduit. The delimited central high-resistivity region and the bounding uninsulated distal lesser-resistivity elements thus collectively form a hydrodynamically smooth volumeter conduit, in which the electric and hydrodynamic fields of the traditional volumeter conduit are advantageously amended in the manner above noted. According to an alternative embodiment, the delimited central region of the improved volumeter conduit is defined by a traditional conduit wafer, i.e., a dielectric wafer containing a central circular conduit as described in U.S. Pat. No. 2,985,830 or U.S. Pat. No. 3,771,058, and the distal elements of lesser resistivity are defined by uninsulated, electrically conductive, circular collars attached to opposite sides of the conduit wafer. Each collar is made to have an outer diameter equal to at least four times, and a thickness between one to three times, the diameter of the conduit in the conduit wafer. Each collar has a central opening which is dimensioned and shaped to precisely conform to the conduit in the conduit wafer, and the collars are arranged on opposite sides of the conduit wafer so that the respective collar openings overlie and remain congruent with the entry and exit orifices of the conduit therein. The conduit in the conduit wafer and the openings in the conductive collars thus collectively form a hydrodynamically smooth volumeter conduit, in which the electric and hydrodynamic fields of the traditional volumeter conduit are advantageously amended in the manner above noted. Volumeter assemblies according to these or other embodiments of the field-amending concept may be adapted by prior-art methods to enable simultaneous passage of a suitable suspension of the particles to be analyzed and an electrical excitation current through the field-amending conduit.

Yet another aspect of the invention is the provision of an improved method for sensing and characterizing particles in which the particles to be characterized are suspended in a liquid medium having an electrical impedance per unit volume which differs from that of the particles and passed substantially one at a time through the field-amending volumeter conduit of the invention while changes in a pre-established electrical current through such conduit are monitored.

The invention and its advantages will be better understood from the ensuing detailed description of preferred embodiments, reference being made to the accompanying drawings in which like reference characters denote like parts.

BRIEF DESCRIPTION OF THE DRAWINGS

FIG. 2 illustrates a longitudinal section through the conduit and particle-sensitive zone of a traditional volumeter conduit wafer;

FIGS. 4A–4D illustrate a series of exemplary current pulses produced by particles transiting the FIG. 2 apparatus on the various trajectories shown therein;

FIG. 7 illustrates a longitudinal section through the conduit and particle-sensitive zone of the volumeter assembly of the invention;

DETAILED DESCRIPTION OF PREFERRED EMBODIMENTS

As noted above, an important object of this invention is to provide an improved apparatus for sensing and characterizing particles, of the type which operates according to the aforementioned Coulter principle.

EMBODIMENT 1

Figure 6:
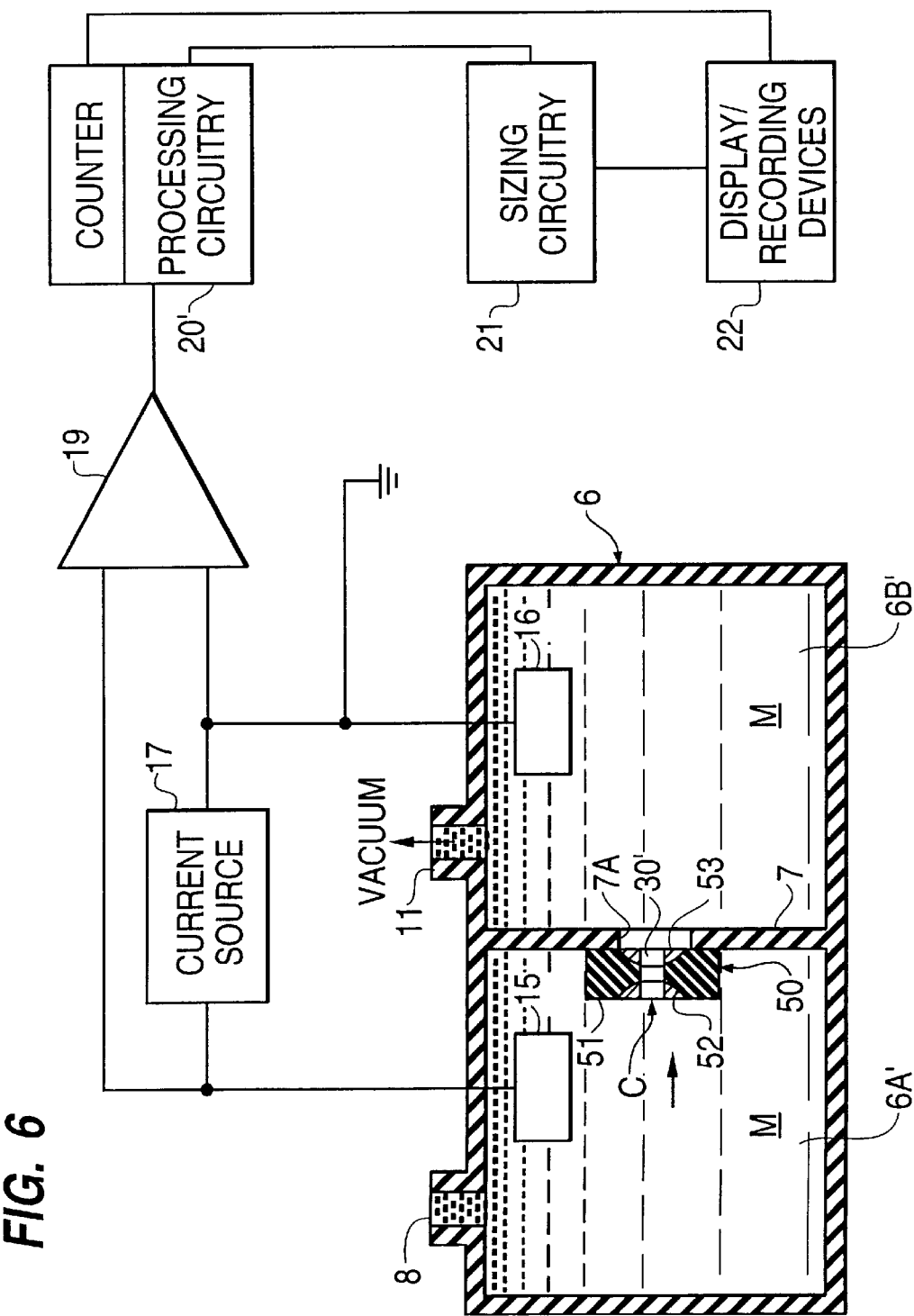
FIG. 6 illustrates the new apparatus for sensing and characterizing particles by the Coulter principle.

In FIG. 6 is schematically illustrated, in accordance with a preferred embodiment of the invention, an improved apparatus for sensing and characterizing particles, one which advantageously combines accuracy in characterization results with simplicity in apparatus construction. Like the prior-art apparatus of FIG. 1, the apparatus of the invention preferably comprises a dual-compartment dielectric vessel 6 containing a wall 7 of dielectric material separating compartments 6A' and 6B', each of which is filled with a particle-suspending liquid medium M (e.g., isotonic saline solution) and each of which contains a respective excitation electrode 15 or 16. Whereas the FIG. 1 apparatus comprises a conduit wafer W incorporating volumeter conduit 10, the FIG. 6 apparatus comprises a volumeter assembly 50 incorporating improved volumeter conduit C. Although volumeter assembly 50 may be made to constitute wall 7, it is preferably provided as an independent structure, e.g., as a disc of appropriate dimensions. Volumeter assembly 50 is mounted over relatively large opening 7A in wall 7 and is substantially surrounded by and immersed in the particle-suspending medium M filling the compartments of vessel 6. A small through-hole transpiercing volumeter assembly 50 provides an improved volumeter conduit C which is caused to constitute the only operative electrical and fluidic connection between compartments 6A' and 6B'. As is discussed in detail below, the novel structure of volumeter assembly 50 is caused to provide conduit C with a delimited central element of high electrical resistivity which is smoothly contiguous on both its axially opposing boundaries to distal elements of substantially lesser resistivity.

In operation, a conventional current source 17 electrically connected to excitation electrodes 15 and 16 establishes an appropriate nominal current flow through improved conduit C, while an appropriate vacuum applied to port 11 simultaneously establishes a flow of particle suspension (introduced into inlet port 8) from compartment 6A' through conduit C into compartment 6B'. Conduit C constricts both the electric and hydrodynamic fields so established in vessel 6, so that wall 30' of conduit C surrounds and defines the flows of particle suspension and electric current between compartments 6A' and 6B'. It is preferred that current source 17 be a constant-current source so that the current it supplies is substantially independent of changes in impedance between electrodes 15 and 16 (e.g., due to substitution of conduits C having different diameters or lengths, temperature-induced changes in the resistivity of particle-suspending medium M, or substitution of suspending medium M having a different resistivity), but current source 17 may less preferably be a voltage source having a high internal impedance. Also electrically connected to electrodes 15 and 16, conventional circuitry 19, 20', and 21 operates to sense, monitor, and process current pulsations in conduit current as occasioned by the more or less individual passage of particles through conduit C, and conventional devices 22 operate to display or record particle count and characteristic data. It is preferred, but not required, that AC-coupled sensing circuit 19 have low input impedance compared to the conduit impedance. In brief, except for volumeter assembly 50 and the advantages to apparatus make-up resulting from the functional properties of conduit C thereof, the apparatus of FIG. 6 is substantially a prior-art apparatus of FIG. 1, e.g., one described in U.S. Pat. No. 2,656,508 or U.S. Pat. No. 3,259,842.

Figure 1:
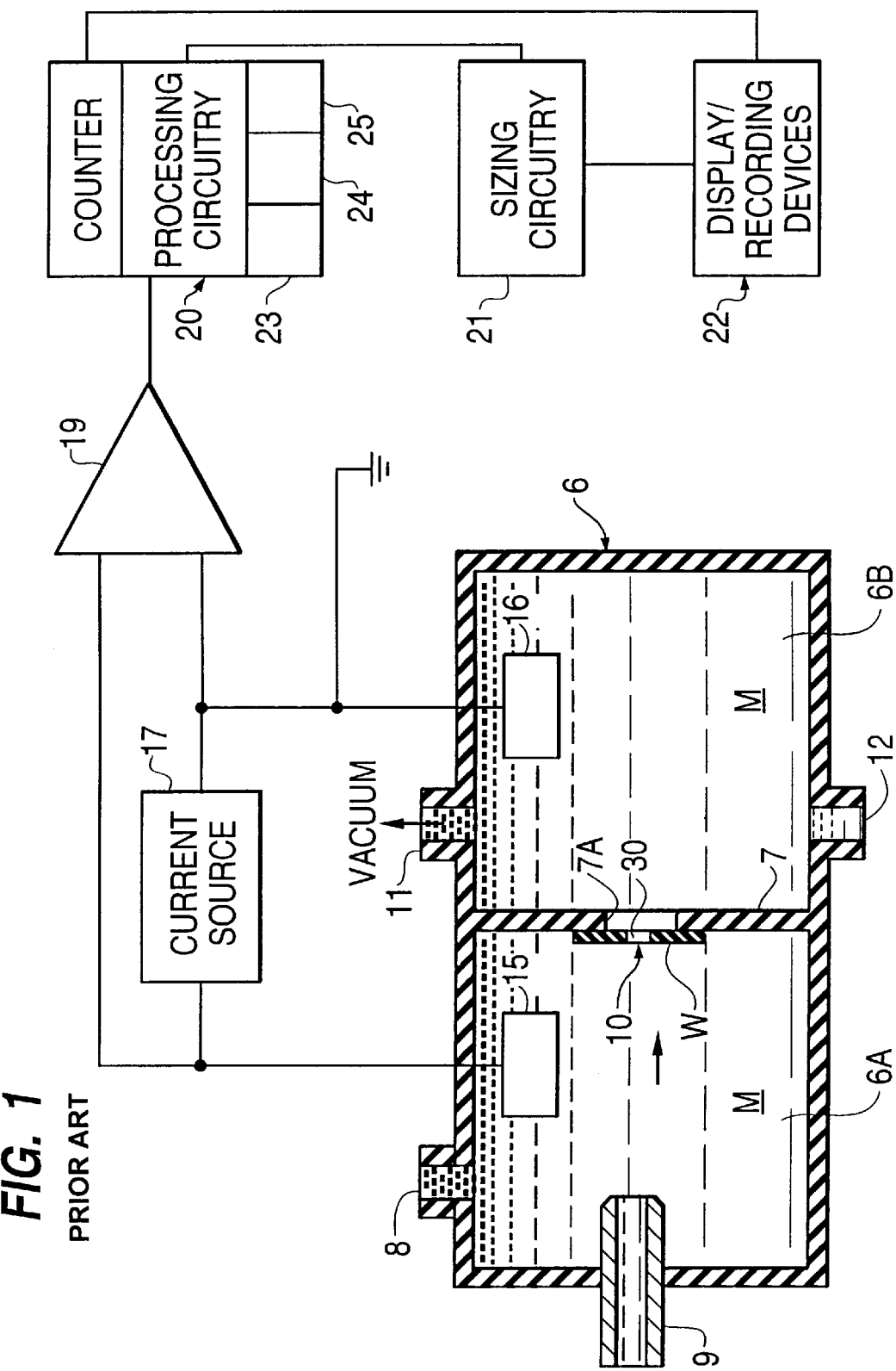
FIG. 1 illustrates a prior-art apparatus for sensing and characterizing particles by the Coulter principle.

However, the novel properties of conduit C enable the apparatus of FIG. 6 to provide substantially the same accuracy in particle characterization data as the prior-art apparatus of FIG. 1, but without requiring the facilitating fluidic subsystems associated with features 9 and 12 or the facilitating pulse-editing and deletion circuits 23, 24, and 25 of FIG. 1. These commercially significant omissions from FIG. 1 are indicated by primed features 6A', 6B', and 20' in FIG. 6. As will be discussed, data inaccuracies due to anomalous pulses from particles on near-wall trajectories are substantially reduced by several mechanisms, and in all but the most demanding applications the complex hydrodynamically-focused flow subsystem driving director 9 in FIG. 1 and anomalous pulse-edit circuit 25 in FIG. 1 can both be omitted from the FIG. 6 apparatus. Extraneous volumetric distributions due to recirculating particles are substantially eliminated, so the sweep-flow subsystem driving port 12 in FIG. 1 and the recursor pulse-edit circuit 24 in FIG. 1 can also both be omitted from the FIG. 6 apparatus. Because functional sample dilution can be avoided by omission of said auxiliary fluidic subsystems in FIG. 1, particle concentration may be readily determined in the FIG. 6 apparatus by positive-displacement methods, e.g., such as described in U.S. Pat. No. 2,869,078. Because pulse deletions due to recirculation or anomalous pulses can be avoided in the FIG. 6 apparatus, required sample volumes and processing times may be reduced. Further, coincidence-correction circuit 23 in FIG. 1 can also be omitted in many applications of the FIG. 6 apparatus, while other applications requiring higher processing rates may benefit from simplified forms of this circuit; since post-collection pulse deletions can be minimized, required sample volumes and processing times may be further reduced. In addition, other operational advantages result from the significantly reduced coincidence volume provided by conduit C, i.e., greater sample throughput rates can be used for a given detectability threshold and level of coincidence artifact, or to decrease clogging concerns a larger-diameter conduit can be used for a given volumetric sensitivity. Thus, improved volumeter conduit C permits elimination of much complex facilitating prior art from the FIG. 1 apparatus, without significant data inaccuracies, whereby the new apparatus of FIG. 6 offers important operational advantages, better cost effectivity, greater reliability, and other commercial advantages. These advantages owe to the novel properties of conduit C, which originate in a characteristic axial variation in axisymmetric electrical resistivity through the novel structure of volumeter assembly 50 in which conduit C is formed.

In accordance with the present invention, the FIG. 6 apparatus is characterized by a volumeter assembly 50 which provides novel functional properties originating in the electrical properties of the solid material from which it is constructed. The material composing volumeter assembly 50 is transpierced by a small through-hole of appropriate cross-section (not necessarily constant) the hydrodynamically smooth wall 30' of which defines conduit C. The axis of conduit C coincides with the intended direction of flow therethrough and is preferably made to coincide with that of volumeter assembly 50. The electrical resistivity of the solid material of which volumeter assembly 50 is formed is, in the broadest sense, made to vary in a substantially axisymmetric manner along the axis of conduit C. Specifically, the electrical resistivity of the solid material surrounding conduit C is preferably so selected as to cause any longitudinal section of volumeter assembly 50 including the axis of conduit C to effectively comprise an axisymmetric, delimited central region of high electrical resistivity which is smoothly contiguous on both its axially opposing boundaries to distal regions of substantially lesser electrical resistivity. Consequently, hydrodynamically smooth wall 30' of conduit C is made to have axisymmetric electrical resistivity which is caused to effectively vary in a desired manner along the axis of the conduit, whereas wall 30 of conduit 10 in homogeneous conduit wafer W of the FIG. 1 apparatus is only required to be hydrodynamically smooth. Such axial gradients in axisymmetric resistivity may be induced, e.g., by suitably doping an appropriate high-resistivity solid member to form regions of effectively lesser resistivity therein, or through mechanical assembly and joining of individual discrete layers or elements having appropriate unequal but substantially uniform individual resistivities into a composite solid material.

The characterizing resistivity profile through the material composing volumeter assembly 50 is preferably realized by causing a common separating layer or element 51, composed of solid material of resistivity substantially greater than that of suspending medium M in which the particles to be characterized are suspended, to be smoothly contiguous and unitary with respective axially-distal layers or elements 52 and 53, each of said distal layers or elements being composed of uninsulated solid material of resistivity substantially less than that of suspending medium M. (The terms "layer" or "element" will hereinafter be used interchangeably to indicate such discrete components of volumeter assemblies.) It is preferred that conduit C comprise a continuous wall 30' defining a right cylindrical conduit of circular cross-section through volumeter assembly 50, i.e., wall 30' is a bore-wall and the conduit cross-section is constant along the axis. Less preferably, prismatic or non-constant conduit cross-sections may be advantageous in some applications of such volumeter assemblies.

With reference now to FIG. 7, conduit C is thus defined by a continuous, hydrodynamically smooth wall 30' collectively comprising sequential wall portions through elements 52, 51, and 53, the contiguous complementary surfaces of elements 52 and 51 forming hydrodynamically smooth delimiting boundary 54, and those of 51 and 53 forming hydrodynamically smooth delimiting boundary 55, respectively, between the portions of conduit C bounded by the respective elements 52, 51, and 53. Each said wall portion of conduit C is thus circumferentially bounded by the uninsulated solid material composing the respective element and smoothly contiguous at delimiting boundaries 54 and 55, respectively, to a congruent adjacent wall portion. Consequently, the characteristic electrical resistivity of defining wall 30' is caused to be substantially axisymmetric, but is made to have significant axial gradients at delimiting boundaries 54 and 55 along the length of any longitudinal section of conduit C. The characterizing axial variation in axisymmetric resistivities substantially originates in the characteristics of the solid materials selected for the make-up of volumeter assembly 50, although geometries of individual elements may be caused to augment certain properties of conduit C. As will be apparent to those skilled in the appropriate arts, volumeter assemblies incorporating the characteristic axial variation in axisymmetric resistivity of wall 30' may be embodied by a variety of techniques in a broad range of designs, geometries, and materials.

Figure 5:
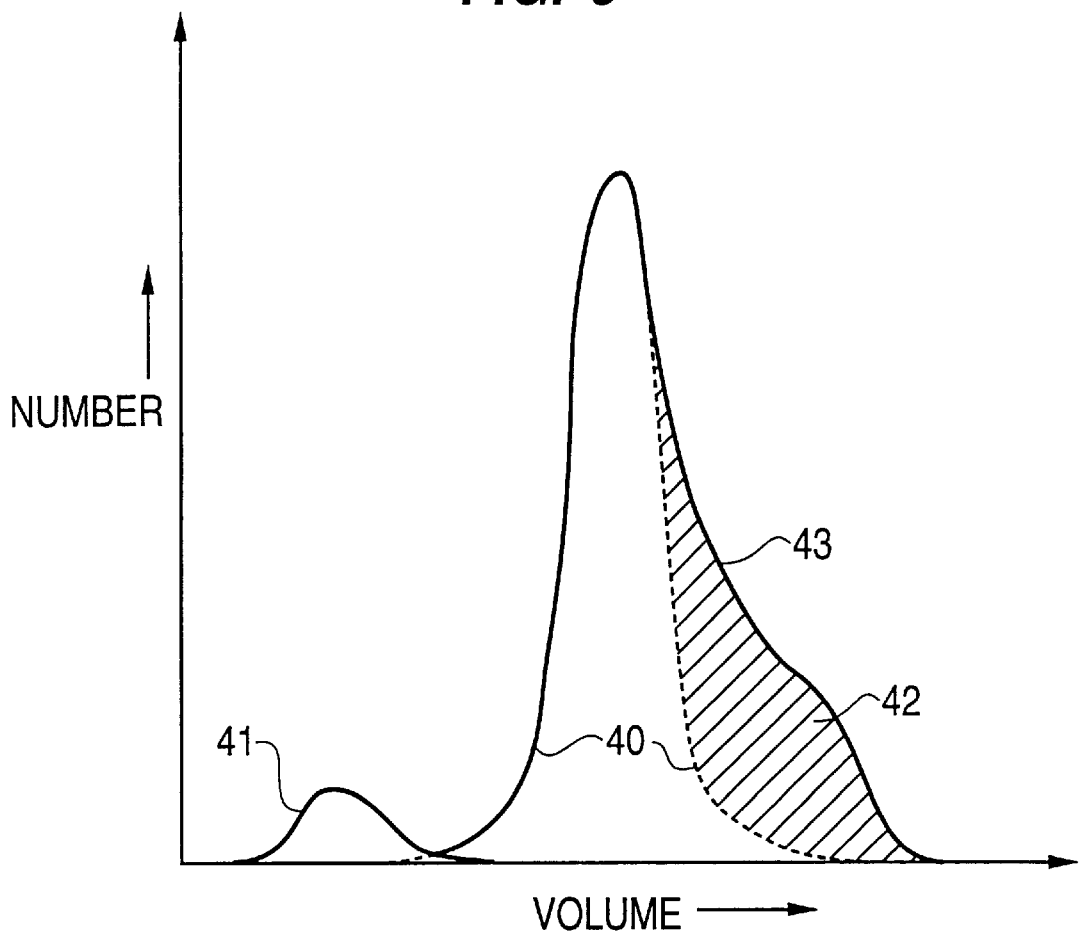
FIG. 5 consists of superimposed histograms illustrating the degrading effects of the anomalous and extraneous pulses of FIGS. 4B–4D.

As with the prior-art apparatus of FIG. 1, characteristics of signal pulses generated by particles passing through conduit C of FIG. 6 result from a complex interaction of the particles with both the electric field established in the suspending medium M by the excitation current between electrodes 15 and 16 and the hydrodynamic field established by the particle-suspending medium M carrying the particles through conduit C. Under influence of the electric field established by the current between electrodes 15 and 16 (and without connection to any external electrical circuitry), uninsulated distal elements 52 and 53 assume individual potentials over their surfaces which directly superimpose independent equipotentials in the vicinity of conduit C. As will be described in detail below, the distribution of the resultant electric field making up particle-sensitive zone Z' in FIG. 7 depends on conduit diameter D' and axial length L' of conduit portion 10', whereas the distribution of the resultant hydrodynamic through-field depends on D' and the cumulative length (L'+$L_1$+$L_2$) of conduit C, where $L_1$ and $L_2$ are the dimensions along wall 30' of elements 52 and 53, respectively. It has been found that the diameter D' and length L' of conduit portion 10' can be selected to provide specific electrical characteristics in sensitive zone Z' of conduit C and that (without adversely affecting the electrical characteristics of the sensitive zone) nonminimal lengths of $L_1$ and $L_2$ of elements 52 and 53 can be made to facilitate quasi-laminar flow through the sensitive zone so as to significantly increase the proportion of particles per second transiting the substantially homogeneous areas of the sensitive zone. Consequently, it has been found that effects of the electric and hydrodynamic fields on pulses generated by particles transiting sensitive zone Z' of volumeter conduit C can be independently optimized. This is in distinct contrast to the prior-art apparatus of FIG. 1, in which conduit wafer W is constructed of homogeneous dielectric material so that wall 30 defining conduit 10 in FIG. 2 is of uniformly high electrical resistivity, and the electric and hydrodynamic fields in conduit 10 are consequently co-determined by the conduit diameter D and the thickness L of the conduit wafer W. Some relevant field properties of improved volumeter conduit C in FIG. 7 can now be contrasted with those aforementioned ones of the FIG. 2 conduit 10:

1. Due to their immersion in the particle-suspending liquid medium M surrounding volumeter assembly 50 and filling conduit C, uninsulated distal elements 52 and 53 of volumeter assembly 50 in FIG. 7 assume individual potentials over their surfaces which impose new field distributions in the axisymmetric electric field established by the current through the conduit. For axial lengths $L_1$ or $L_2$ of elements 52 or 53 greater than approximately the conduit diameter D', the resultant electric field external to conduit C (i.e., between electrodes 15 and 16 and elements 52 and 53, respectively, in FIG. 6) is essentially homogeneous. The axisymmetric field regions between ambit fields 31' and 32' and the external fields, indicated by equipotentials 56 and 57, are substantially at the potential of the respective element 52 or 53 and are of very low field strength and gradient. These equipotential regions serve to functionally isolate ambit fields 31' and 32' from the external electric field so that the ambit fields are totally confined within volumeter conduit C. The resultant particle-sensitive zone Z' functionally includes conduit portion 10' between delimiting boundaries 54 and 55, plus the two semielliptical ambit electric fields 31' and 32' coaxial with and extending outside said delimiting boundaries into portions of conduit C circumferentially bounded by elements 52 and 53. Thus, portion 10' of conduit C provides a consistent reference volume against which the volume of liquid displaced by particles may be compared and is therefore functionally analogous to traditional Coulter volumeter conduit 10 in FIGS. 1 and 2. Analogously to the traditional Coulter conduit, the distribution of the resultant electric field making up sensitive zone Z' depends on conduit diameter D' at boundaries 54 and 55 and axial length L' of conduit portion 10', while the semielliptical equipotentials corresponding to the desired detectability threshold determine the effective spatial extent of ambit fields 31' and 32'. It has been found that the minimum axial lengths $L_1$ and $L_2$ of elements 52 and 53 can be selected according to the desired detectability threshold in particle size. Consequently, lengths $L_1$ and $L_2$ are made at least equal to the axial extent of the threshold ambit electric fields of a traditional Coulter volumeter conduit having diameter D equal to the diameter D' of functional Coulter conduit 10', or for a one percent detectability threshold, $L_1$=$L_2$=D'. (However, $L_1$ and $L_2$ may be increased above these minimal lengths to improve conduit hydrodynamics through sensitive zone Z'; vide infra, Item 3.) For $L_1$=$L_2$=D', it has been found that the effective ambit fields extend outward from the respective entrance and exit boundaries 54 and 55 of functional Coulter conduit 10' approximately D'/2, with equal lateral intercepts, for a one-percent detectability threshold; these dimensions compare to D and 1.15D, respectively, for the traditional Coulter conduit. It can be shown that the portion of particle-sensitive zone Z' within the functional Coulter conduit 10' is (L'/D')/(L'/D'+16K'/3), where K' is now the product of the three diameter-normalized intercepts of the chosen threshold equipotential on a coordinate system with axial origins at the center of particular boundary 54 or 55. For the one-percent equipotentials 35' and 36', the axial length of sensitive zone Z' is (L'+D'), K'=0.125, and for L'/D'=1.2, only 36 percent of the sensitive zone is external to the functional Coulter conduit 10'; these values compare to (L+2D), K=1.325, and 85 percent, respectively, for a traditional Coulter conduit of the same diameter and length. Thus, for equivalent functional dimensions and a detectability threshold of one percent, the ambit portion of the sensitive zone Z' for improved volumeter conduit C is approximately 0.095, and its coincidence volume 0.226, of that for the comparable Coulter conduit; for conduits with L'/D'=0.75=L/D, the ratio of coincidence volumes is 0.180. The smaller coincidence volume of volumeter conduit C reduces the occurrence of misshapen pulses due to simultaneous passage of multiple particles and so removes some artifactual skewness (42 in FIG. 5) from the particle histogram. Volumetric sensitivities are inversely proportional to coincidence volumes and so are improved in conduit C by a factor of 5.51.

2. The electric field within functional Coulter conduit 10' is similar to that within the traditional Coulter conduit. However, indirect data based on characteristics of particle pulses suggest that midpoint homogeneity within this part of particle-sensitive zone Z' is achieved for axial lengths of this portion about 20 percent less than for a traditional Coulter conduit of equivalent cross-sectional geometry. More importantly, these data also indicate that the orifice gradients of sensitive zone Z' are confined to the annular region adjacent to the conduit wall 30' and outside the radius r'=0.85(D'/2), compared to r=0.75(D/2) for the traditional Coulter conduit, i.e., the cross section of functional Coulter conduit 10' through which particles can transit without producing an anomalous pulse is larger than for a traditional Coulter of comparable functional dimensions. For a given degree of anomalous pulse amplitude or a specified nonlinearity in volumetric response, the cross-sectional area through which particles can transit particle-sensitive zone Z' of the improved volumeter conduit C may be approximately 28 percent greater than for the traditional Coulter conduit of equivalent geometry. These favorable and unexpected electric-field modifications combine with the hydrodynamic findings of Item 3 in an advantageous manner.

Figure 3:
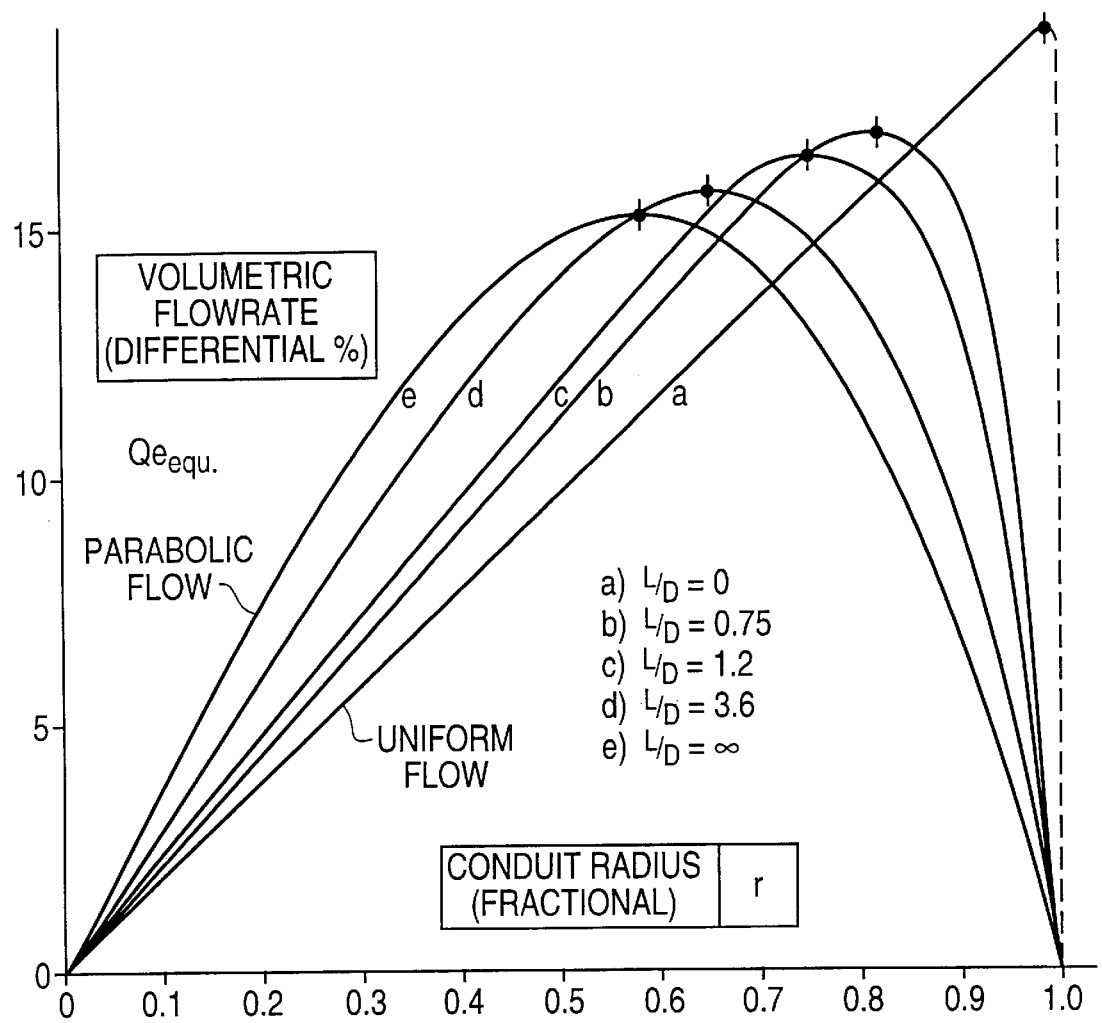
FIG. 3 illustrates the hydrodynamic effects of increasing the L/D ratio of a circular conduit for common particle-suspending liquids.

3. Hydrodynamic characteristics not available with traditional Coulter conduits may be provided in improved volumeter conduit C by making the axial lengths $L_1$ and $L_2$ of elements 52 and 53 greater than the minimum required to achieve the aforesaid electrical effects on the particle-sensitive zone, i.e., greater than D'. As has been noted, the frequency of anomalous pulses (e.g., those of FIG. 4B or 4C) depends on the portion of the conduit cross-section occupied by the orifice gradients of the sensitive zone and on the radial position of the modal particle trajectories through it. For a given conduit the range of radial positions of the modal trajectories lies between the radial positions of the entry and exit modal trajectories, while the mean radial position lies at approximately one-half the sum of these positions. In traditional Coulter conduit 10 of FIG. 2, the entry modal trajectory for particles of diameter p overlies the shear layer near the wall, at r=(D−p)/2 approximately, and the position of the exit modal trajectory is determined by the length L of the conduit 10, as shown in FIG. 3. Thus, while the average radial position of the modal particle trajectories may be moved inward out of the high-gradient wall fields as in the prior long-conduit art, improvement is limited by the near-wall position of the modal trajectories in the quasi-uniform entry flow. In conduit C of FIG. 7, the length $L_1$ of element 52 permits the quasi-uniform velocity profile of the entry hydrodynamic field to develop into quasi-laminar flow through the particle-sensitive zone Z'. As noted, the degree of laminarity $\xi$ is inversely proportional to the Reynold's number $\mathfrak{Re}$, i.e., $\xi$ x'/(R' $\mathfrak{Re}$), where x' is now the distance into conduit C from the entry orifice 33' and R'=D'/2. At the entry 33' of conduit C in FIG. 7, x'=0, and the flow-velocity profile is quasi-uniform (a in FIG. 3); for small particles the annular portion of the conduit cross-section containing the modal particle trajectories lies near the conduit wall 30'. However, downstream in conduit C, at boundary 54 of functional Coulter conduit 10', x' equals the axial length $L_1$ of element 52 in FIG. 7, with two significant hydrodynamic results. First, effects due to edge curvature and imperfections are less significant than with the traditional Coulter conduit, since these are smoothed in the developing quasi-laminar flow. Most significantly, in contrast to the prior conduit art, it has been found that the degree of such laminarity may be selected to control the mean and dispersion of the radial positions of modal particle trajectories through the sensitive zone Z' of conduit C. In FIG. 3 are shown results of volumetric flowrate calculations for L/D=0.75 (b), 1.20 (c), and 3.60 (d), the peaks (dotted) of which curves represent the modal particle trajectories. Now, if length $L_1$ of element 52 is selected so that $L_1$=1.2D'=x', the entry modal trajectories through the functional Coulter conduit 10' occur (c in FIG. 3) in the annulus centered at r'=0.76 (D'/2); and if the axial length L' of functional Coulter conduit 10' is 0.75D', the exit modal trajectories into element 53 can similarly be shown to be at r'=0.72(D'/2) for the cumulative conduit length x'=(L'+$L_1$)=1.95D'. Both entry and exit modal trajectories are consequently well inside the radius r'=0.85(D'/2) at which the intense electric-field gradients begin, and substantially fewer particles interact with the smaller inhomogeneous fields near wall 30' to cause skewness in the volumetric distribution (42 in FIG. 5). Such conduits C for which L'/D'>0.75 produce exit modal trajectories lying inside r'=0.72(D'/2), and the frequency of anomalous pulses is further decreased. Further, since significant laminarity has developed for $L_1$=3.6D' (d in FIG. 3), modal trajectories can be positioned as closely as desired to the limiting laminar position for practical lengths $L_1$ of region 52, regardless of the length L' of the functional Coulter conduit 10'. Thus, through use of differential volumetric flow data such as illustrated in FIG. 3, an appropriate $L_1$ for the element 52 may be selected so that particle-sensitive zone Z' is located in a specific portion of the volumeter conduit C to achieve a desired radial position of the modal particle trajectory; further, due to the smaller sensitive zone Z' provided by conduit C, this important advantage can be achieved for lengths L' of functional Coulter conduit 10' shorter than practicable with traditional Coulter conduits. Alternatively, by selecting an appropriate ratio of length $L_1$ of element 52 to the length L' of functional Coulter conduit 10', the dispersion of the radial positions of the modal trajectories about the mean modal-trajectory position may be optimized. While the length $L_2$ of element 53 permits further transition toward fully-developed laminar flow and so may decrease turbulence effects in the jetting zone, its primary function is to isolate the exit ambit 32' of particle-sensitive zone Z' so that recirculating particles cannot recurse into it and generate extraneous pulses. However, length $L_2$ of element 53 of volumeter conduit C may be selected to provide a desired relationship between the pressure differential across conduit C and the average flow velocity through the sensitive zone Z' within conduit C.

4. As with the traditional Coulter conduit, particles entering volumeter conduit C on near-axial trajectories, e.g., $A_T$ in FIG. 2, generate pulses similar to the pulse of FIG. 4A. However, particles entering conduit C in the outer extents of the developing converging flow will be accelerated around the conduit edge 33' in FIG. 7 and through the annulus near wall 30' of the element 52 where the developing laminar tubular flow serves to straighten the trajectories of such particles, thereby eliminating particle trajectories (e.g., $B_T$ or $C_T$ in FIG. 2) curving through the particle-sensitive zone Z' of conduit C and causing anomalous pulses similar to those in FIG. 4B or 4C. The number of particles potentially giving rise to such anomalous particle pulses can be further decreased by increasing the length $L_1$ of element 52, while the number of pulses similar to B can be decreased by increasing the length L' of element 51. By these combined means, skewness 42 in the volumetric distribution of FIG. 5 may be substantially eliminated. Moreover, since the exit ambit 32' in FIG. 7 is contained within the portion of conduit C bounded by element 53, decelerating particles that have exited conduit C are separated from ambit 32' by the low-strength field region 57 and cannot be drawn back into the ambit (by, e.g., trajectory $D_T$ in FIG. 2) as the particle-suspending liquid recirculates into the toroidal low-pressure region surrounding the exit jet. Thus, no extraneous pulses of low amplitude and long duration (e.g., the pulse in FIG. 4D) can be generated, and the secondary volume distribution (41 in FIG. 5) below the actual sample distribution (40 in FIG. 5) is eliminated.

In summary, through a characteristic axial variation in axisymmetric wall resistivity, conduit C provides novel field and functional properties originating in the selection of materials surrounding conduit C and composing volumeter assembly 50. These advantages substantially originate in the resulting axisymmetric pattern of electrical resistivities through the solid material in which conduit C is formed, rather than in any specific combination of element geometry or combinations of particular materials. Specifically, central high-resistivity element 51 of volumeter assembly 50 in FIGS. 6 and 7 defines in conduit C a functional Coulter conduit 10'. The axial dimensions of uninsulated distal elements 52 and 53 of volumeter assembly 50 in FIGS. 6 and 7 can be selected so these lesser-resistivity elements independently function to amend both the electric and hydrodynamic fields in the vicinity of the volumeter conduit C by: (i) shaping the electric field resulting from the excitation current so as to substantially confine the particle-sensitive zone Z' in FIG. 7 within the physical boundaries of conduit C to form functional Coulter conduit 10'; and (ii) enabling development of quasi-laminar flow through sensitive zone Z' so as to significantly increase the proportion of particles per second transiting the substantially homogeneous areas of said sensitive zone. As one advantageous consequence, the isolated sensitive zone Z' of functional Coulter conduit 10' can be made substantially insensitive to particles entering conduit C on high-angle trajectories and to particles exiting conduit C on recirculating trajectories. As another advantageous consequence, sensitive zone Z' of functional Coulter conduit 10' is substantially smaller than for the traditional Coulter conduit of comparable dimensions; in addition, while the dimensions of the functional Coulter conduit 10' can be selected substantially as would be those of a traditional Coulter conduit, the range of permissible dimensions is substantially increased. As yet another advantageous consequence, functional Coulter conduit 10' can be made to demonstrate hydrodynamic characteristics usually associated with the prior-art method of hydrodynamically focused flow. Central to this advantage is the finding that contrary to the prior art, fully-developed laminar flow [corresponding to (e) in FIG. 3] is not necessary to provide the desired characteristics thereby obtained, viz., that indeed quasi-laminar flow such as occurs in tubular flows having lesser length-to-diameter ratios [e.g., (d) or (c) in FIG. 3] may be made to provide these characteristics to a practical degree through static means, if sensitive zone Z' can be decoupled from the hydrodynamic length of the conduit. This latter property is enabled through the aforementioned characteristic axial variation in axisymmetric resistivity along the wall of conduit C. In addition, said resistivity characteristic directly reduces the radial extent of the high-gradient portions of sensitive zone Z', decreasing the degree of laminarity required to achieve a desired degree of volumetric inaccuracy due to pulses on near-wall trajectories. Together, the two consequences of lesser-resistivity elements 52 and 53 permit accuracies in volumetric data comparable to those provided by the best FIG. 1 apparatus, but without the facilitating prior art required by the FIG. 1 apparatus.

It is preferred that volumeter assembly 50 in FIG. 7 comprise elements 51, 52, and 53, and this is necessary if particle-sensitive zone Z' of conduit C is to be substantially symmetric about its axial midpoint. It is preferred that the axial length of both elements 52 and 53 be at least approximately equal to the diameter D' of functional Coulter conduit 10' so that sensitive zone Z' is made substantially independent of the cumulative length of conduit C, and this is necessary if the effects of electric and hydrodynamic fields on particle-pulse characteristics are to best be optimized. It is preferred that L'/D' be in the range between 0.2 and 2.5. Generally, respective axial lengths $L_1$ and $L_2$ of elements 52 and 53 between one to four times the diameter D' of functional Coulter conduit 10' are preferred; longer lengths for element 52 may be useful in establishing a desired position of modal particle trajectories through said functional Coulter conduit, while longer lengths for element 53 may be useful in establishing a desired pressure/flow-rate relation for conduit C. Axial lengths of elements 52 and 53 somewhat less than the diameter D' of the functional Coulter conduit 10' may be used if detectability thresholds greater than approximately one percent are acceptable and anomalous pulses are of small concern. Some of the advantages of this invention may be obtained through use of only a single element 52 or 53 arranged at, respectively, the entry or exit of the functional Coulter conduit 10' in volumeter assembly C of FIG. 7. Thus, if the concern is reduction of histogram skewness (42 in FIG. 5) due to particles transiting the sensitive zone near the conduit wall, element 53 could be omitted, the asymmetric ambit fields of sensitive zone Z' then resembling 31' in FIG. 7 on the entry side and 32 in FIG. 2 on the exit side; element 52 will reduce occurrence of anomalous pulses, but recirculating particles near the exit of the dual-element volumeter assembly will produce extraneous pulses and a low-volume distribution (41 in FIG. 5). Conversely, if the concern is elimination of the volume distribution (41 in FIG. 5) due to recirculating particles, element 52 could be omitted and the asymmetric ambit fields of sensitive zone Z' will resemble 31 in FIG. 2 on the entry side and 32' in FIG. 7 on the exit side; element 53 will reduce the occurrence of recirculation pulses, but particles transiting the conduit of the dual-element volumeter assembly near its wall will produce histogram skewness (42 in FIG. 5) due to anomalous pulses. It is preferred that volumeter assembly 50 comprise elements 51, 52, and 53.

The novel functional properties provided by volumeter conduit C in FIG. 6 originate in the aforementioned axial variation in axisymmetric resistivity through the material of which volumeter assembly 50 is constructed. Volumeter conduits incorporating field-amending characteristics may be embodied in numerous dissimilar constructions. Because the resistivity of elements 52 and 53 must be less than that of the particle-suspending medium M, because the wall 30' of conduit C must be substantially smooth in the hydrodynamic sense, and because volumeter assembly 50 is desired to be a simple device substantially substitutable for conduit wafer W in a FIG. 1 apparatus, it is preferred that volumeter assembly 50 be constructed from solid material. The characterizing attribute of volumeter assembly 50 is the axial variation in the axisymmetric resistivity through the solid material about the axis of the intended transpiercing conduit C. The combination of axial variation in effective resistivity and hydrodynamic smoothness in wall 30' through the solid material composing volumeter assembly 50 is preferably achieved by appropriately inducing suitable resistivity gradients in the material, transpiercing the volumeter assembly at an appropriate site to form a through-hole, and then appropriately finishing the through-hole to generate the hydrodynamically smooth wall 30' defining conduit C. As will be apparent to those skilled in the appropriate arts, volumeter assemblies incorporating the inventive concepts may be embodied by a variety of techniques in a broad range of forms and materials. The aforementioned resistivity variation may be either made to occur through the solid material about the axis of the intended transpiercing conduit C, e.g., Embodiment 3, or made to occur by the appropriate selection of the individual solid elements 51, 52, and 53 prior to their assembly into volumeter assembly 50, e.g., Embodiments 2 and 4 though 8. In the latter case it is generally preferable that the elements be conjoined in the aforementioned manner prior to transpiercing, although it may be preferable in the case of large-diameter conduits for the elements to be individually transpierced to a smaller diameter, followed by finishing of the conduit in the conjoined elements to the desired conduit diameter.

Regardless of the implementation, it is most important that the conduit C be fluidically continuous and hydrodynamically smooth throughout its length. Due to the need for hydrodynamic smoothness, less preferable are construction methods which rely on either assembly of individual elements prefinished to the final conduit dimensions or use of various mechanical methods for locating and maintaining the elements in their working positions. Although a volumeter assembly 50 may be made to constitute wall 7 in FIG. 6, for constructional reasons conduit C is preferably provided in a volumeter assembly 50 of more convenient dimension and form. Similarly, a discoid or cylindrical form is generally preferable, and it is also preferable that the axis of conduit C be substantially co-axial with that of volumeter assembly 50. For ease of manufacture, it is preferred that all transverse surfaces of elements 51, 52, and 53 be planar, but other design considerations may require that individual elements be made to have other substantially axisymmetric surface geometries, to which any contiguous surfaces are made complementary, e.g., as indicated in FIG. 7. Individual elements 51, 52, and 53 can be given a wide variety of geometries, some of which can secondarily augment the field-shaping properties of the conduit assembled therefrom. Within broad limits the external geometry of elements 52 and 53 is not critical to their primary functions and may be adapted to provide specific characteristics of the new volumeter assembly, e.g., flow matching through a trumpet shape for entry element 52 as in Embodiment 6 or causing element 52 or 53 to constitute part of a containment vessel. In addition, the lateral extent of elements 52 and 53 enables yet other design freedom which will be discussed in connection with Embodiments 4 and 5.

The material used to form elements 51, 52, and 53 is not critical to their primary functions in volumeter assembly 50 and so may be chosen to provide volumeter characteristics required by a particular application. Numerous implementations of the new volumeter are thus possible, of which some will be better suited for use in certain analyses or with particular particle/liquid systems. Element 51 is required to have an electrical resistivity substantially greater than that of the particle-suspending medium M and is preferably made from a dielectric such as ruby, sapphire, alumina, beryllia, synthetic quartz, or other material suited to a given application. However, as discussed in Embodiment 7, element 51 may also be made from a lossy dielectric such as a conductive glass, a conductive ceramic, or a type of conductive polymer or plastic, the resistivity of which is effectively greater than that of the suspending medium M but less than that of the aforementioned dielectrics. Elements 52 and 53 are required to have resistivities substantially less than that of the suspending medium M and are preferably metals or alloys from the platinum group or conductive ceramics such as certain titanium, tungsten, or silicon carbides. Some applications may benefit from use of metals such as gold, silver, titanium tantalum, tungsten, or their various alloys. Still other applications may benefit from use of nickel, copper, or their alloys, either as a metal or as a cermet comprising one of these metals infiltrated into the microstructure of a ceramic such as alumina. Yet other applications may benefit from use of glassy carbon. Elements 52 and 53 need not be of the same material, and some applications of the new volumeter assembly may benefit from a judicious mismatch in one or more material properties. Generally, the materials are preferably homogeneous, but inhomogeneous materials may be preferable in specific applications. As discussed in Embodiment 5, elements 52 or 53 may be formed from one material and coated or plated with another material in order to provide combinations of material properties unobtainable with the individual materials. Some of the above advantages are achieved through the use of more-resistive materials, as for example ones whose resistivity is less than, but approximates, that of the liquid medium M in which the particles are suspended.

It is believed that the concepts of this invention are now sufficiently described that, with the aid of preferred embodiments to follow, those skilled in the relevant arts will be able to fabricate field-amending volumeter assemblies suited to many applications of the Coulter principle. Volumeter assemblies incorporating the field-amending concept may be adapted by prior-art methods to enable simultaneous passage of a suitable suspension of the particles to be characterized and an electrical excitation current through the field-amending conduit. Although the improved conduit may be excited by voltage sources, e.g., as in U.S. Pat. No. 2,656,508, use of constant-current excitation sources such as taught in U.S. Pat. No. 3,259,842 is preferable; the sources may be direct current, alternating current, or a combination thereof. As indicated in Embodiment 8, the invention is adaptable to other forms of apparatus incorporating the Coulter principle, e.g., ones adapted to incorporate other sensing modalities or to sort particles.

EMBODIMENT 2

Volumeter assembly 50 in FIG. 7 may be implemented through mechanical assembly and joining of discrete components into a composite solid assembly composed of individual elements having appropriate unequal but substantially uniform individual resistivities. In an embodiment of particular applicability for volumeter assemblies comprising large conduits (e.g., $D' \geq 0.400$ mm, approximately), element 51 may be a convenient disc preform of highly resistive ceramic powder which is proportional in axial thickness to the desired conduit length according to the intended manufacturing technique. The axial length $L'$ of element 51 is most preferably 0.50 to 2.5 times $D'$. Elements 52 and 53 are inset into complementary concavities in element 51, to conveniently provide the desired axial conduit length $L'$ in a structure of acceptable mechanical strength. Preferably, high-resistivity element 51 is formed of alumina of appropriate grain size and purity, and elements 52 and 53 are made of an appropriate cermet (e.g., alumina infiltrated with nickel or other metal appropriate to the intended application) or one of the conductive ceramics (e.g., titanium carbide). Elements 52 and 53 may be shaped as the spherical segments shown in FIG. 7, or they may be flat discs or other axisymmetric geometries to which the form of the highly resistive central element 51 is adapted. Axial lengths $L_1$ and $L_2$ of elements 52 and 53 are most preferably a minimum of four times the intended diameter $D'$ of conduit C, and the diameter of these elements at the surface of element 51 preferably is approximately five times the conduit diameter $D'$. Complementary elements 51, 52, and 53 may be molded (e.g., by injection processes), sintered, finished to form if necessary, and joined (e.g., by appropriate brazing methods or through use of appropriate metal-filled adhesives) prior to transpiercing and finishing volumeter assembly 50 to the desired conduit diameter $D'$ and lengths $L_1$ and $L_2$ as known in the ceramics-processing or conduit-wafer arts. Preferably, field-amending conduit C will have a constant circular cross-section and be co-axial with volumeter assembly 50. The outer circumferential surface of volumeter assembly 50 may be finished as appropriate. Some combinations of materials may permit unfired preforms to be assembled and sintered to form volumeter assembly 50.

Elements 52 and 53 of volumeter assembly 50 in FIG. 7 may also be either preformed of one of the metallic conductors and appropriately affixed into concavities in element 51 or formed in place therein, e.g., through use of an appropriate metallic-filled adhesive or paint. For example, discs of 1.0 mm thickness may be prepared from a convenient rod of 99.5% purity alumina having grain size in the range between 0.003 mm and 0.005 mm, and centered spherical concavities approximately 0.40 mm deep by 1.0 mm in segment diameter at the surface of the disc are prepared on each side of the discs as is known in the ceramics arts. Each concavity in such resultant element 51 may be either filled with gold-filled adhesive and cured, or given repeated coats of a platinum-filled paint such as used in forming electrodes on glass and fired, according to the appropriate protocol to form a slightly protruding conductive deposit in each concavity. Each disc may then be lapped flat on each surface to form elements 52 and 53, transpierced through the center of the disc, and the through-holes finished to form hydrodynamically smooth circular conduit C having, e.g., D'=0.200 mm, L'≡$L_2$=0.200 mm, and $L_1$≡0.400 mm. Care is required to achieve the desired thickness in elements 52 and 53 without creating voids in the conductive deposits or causing the deposits to break away from element 51 during processing.

It is important that field-amending conduit C be finished (if not formed) after volumeter assembly is formed, so that wall 30' defining the conduit is hydrodynamically smooth. In some applications, volumeter conduits resulting from such implementations may benefit from making element 51 from a lossy ceramic as discussed in Embodiment 7, from providing element 52 a shaped inlet as discussed in Embodiment 6, or from coating or plating the conductive preforms for elements 52 and 53 to provide a combination of material properties not available with the base material as discussed in Embodiment 5.

EMBODIMENT 3

In another embodiment according to FIG. 7, a volumeter assembly 50 of particular applicability for small conduits (e.g., preferably circular, with D'≦0.010 mm, approximately) may be constructed virtually, from a single material, by using suitable doping methods to induce an appropriate resistivity profile. At the site intended for forming the through-hole defining field-amending conduit C, the electrical resistivity of an appropriate solid substrate may be made to effectively vary through the thickness thereof, e.g., to define a central delimited region of high electrical resistivity (approximately equal in thickness to the intended conduit diameter) which is contiguously bounded by distal regions of substantially lesser electrical resistivity (approximately equal in thickness to one to three times the intended conduit diameter). For example, suitable impurity doping methods as known in the semiconductor art may be used to create regions 52 and 53 of substantially lesser resistivity which intersect the surfaces on opposite sides of an intrinsic semiconductor (e.g., silicon) substrate 51 to form exposed regions of diameter approximately five times the conduit diameter. The individual volumeter assemblies 50 may be prepared therefrom and provided with an individual hydrodynamically smooth conduit C as is known in the relevant arts. Delimiting boundaries 54 and 55 in this embodiment are virtual and may be diffuse, rather than discrete as indicated in FIG. 7, but may be made substantially distinct as is known in the integrated-circuit art. The exposed surfaces of regions 52 and 53 must be electrically uninsulated, and all exposed surfaces of volumeter assembly 50 made to be compatible with the liquid medium used to suspend the particles. This embodiment offers advantages for designs incorporating other electronic functions, e.g., as described in U.S. Pat. No. 4,760,328.

EMBODIMENT 4

Figure 8B:
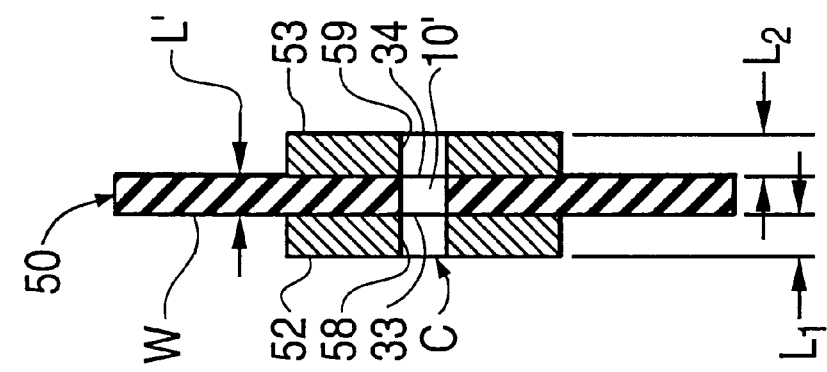
FIGS. 8A and 8B illustrates front and longitudinal-section views of an alternative embodiment of the volumeter assembly of the invention.
Figure 8A:
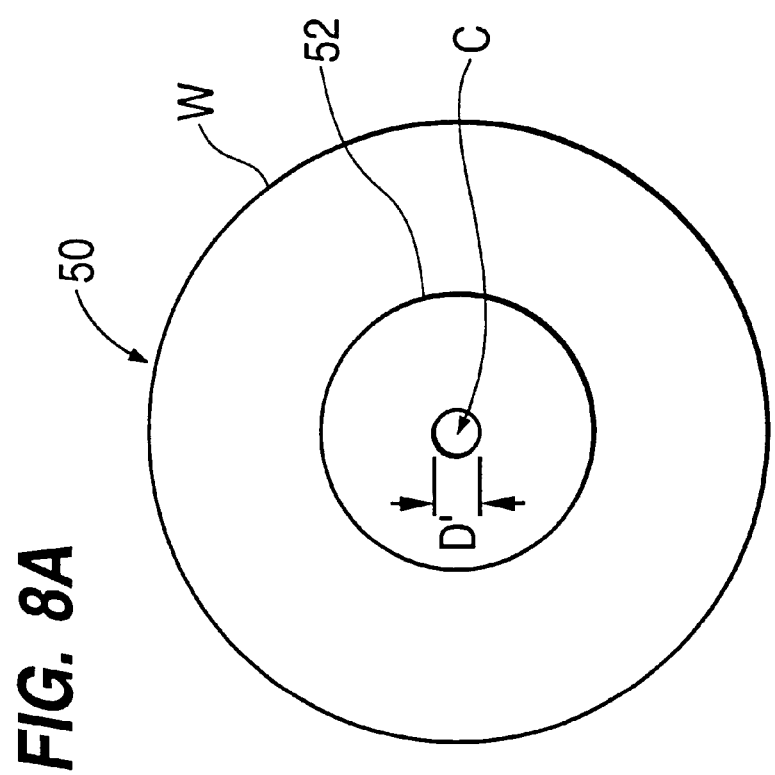

In the above embodiments the lesser-resistivity elements or regions of volumeter assembly 50 are incorporated within the volume envelope of high-resistivity element 51. For mid-range conduit diameters, volumeter assembly 50 may include a pair of electrically conductive collars, each comprising a disc of electrically conductive material having a central opening therein, attached to a dielectric disc of convenient diameter having a central through-hole of suitable dimension. With reference now to FIGS. 8A and 8B, the high-resistivity region of volumeter assembly 50 is preferably a traditional Coulter conduit wafer W, i.e., a ruby or sapphire wafer containing a central circular conduit 10' as described in U.S. Pat. No. 2,985,830 or U.S. Pat. No. 3,771,058. The dimensions of the Coulter conduit wafer W and its geometric conduit 10' may be selected according to the intended application as is known in the art, e.g., appropriate dimensions for leukocyte characterization include an conduit diameter D'=0.100 mm in a ruby wafer 4.0 mm in outer diameter and L'=0.075 mm in thickness. The uninsulated lesser-resistivity elements of the field-amending conduit 50 may preferably be circular collars 52 and 53 made of a platinum alloy or a conductive ceramic such as titanium carbide. Each collar 52 or 53 has a respective central opening 58 or 59 which is dimensioned and shaped to precisely conform to the conduit orifices 33 and 34 of the selected Coulter conduit wafer W. Collar openings 58 and 59 are congruently arranged with respect to the orifices 33 or 34 of the Coulter conduit, and the collars 52 and 53 are so joined to conduit wafer W that the conduit formed by the collar openings 58 and 59 and the Coulter conduit 10' reliably functions hydrodynamically as one smoothly continuous conduit C. Elements 52 and 53 may be joined to conduit wafer W by, e.g., vacuum brazing, commercial epoxy or metal-filled adhesives, use of appropriate glass frits, etc., according to the application. Preferably, field-amending conduit C is formed in situ, and the respective length $L_1$ or $L_2$ of each collar 52 or 53 along the conduit C should at least approximate the diameter D' of the traditional Coulter conduit; most preferably, said lengths may be one to three times the diameter of conduit 10' in Coulter conduit wafer W, whereby the electric and hydrodynamic fields of the traditional volumeter conduit are advantageously amended in the manner above noted.

The outer diameter of the collar discs may preferably be at least approximately five times the diameter D' of the traditional Coulter conduit 10', in which case the electric field in the vicinity of field-amending conduit C is substantially like that for Embodiment 2, shown in FIG. 7. However, this dimension is not critical to the primary functions of the collars and may be chosen to satisfy secondary functions, as will be discussed. Although shown as planar, the configuration of the outer face of collars 52 or 53 in FIG. 8B may be any configuration suited to the application of the particular volumeter assembly. Although the collars are shown as of constant cross-section, the internal longitudinal section of either collar 62 or 53 may be chosen to provide a secondary function as discussed in Embodiment 6 or either of the collars 52 or 53 may form part of a mounting device or of a liquid containment vessel. As has been discussed, some of the advantages of this invention may be obtained through the less preferable use of only a single collar arranged at either the entry orifice 33 or exit orifice 34 of the traditional Coulter conduit 10' in conduit wafer W.

Figure 9:
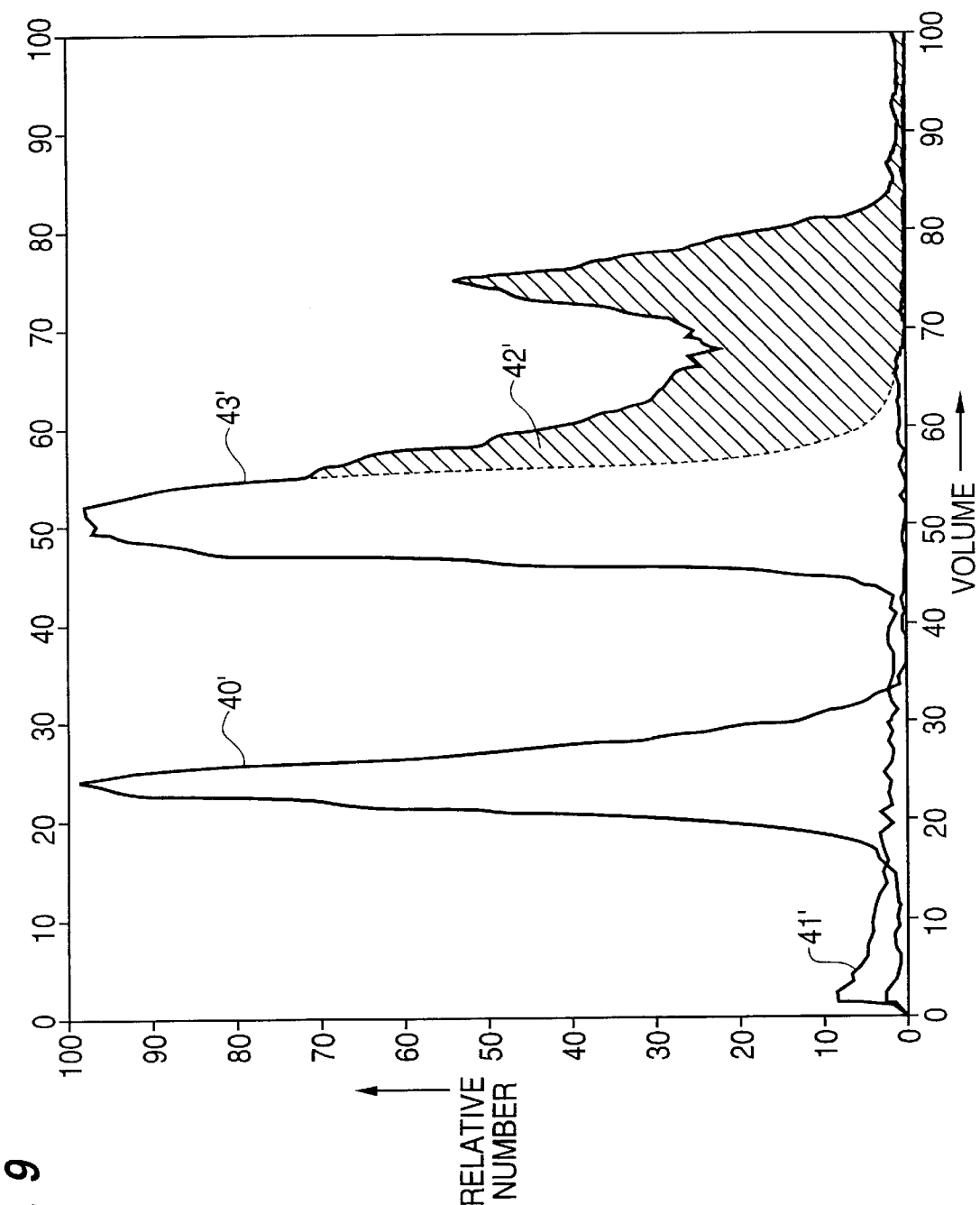
FIG. 9 consists of superimposed histograms illustrating the advantageous effects of the present invention vis-à-vis the prior art.

FIG. 9 illustrates the practical benefits obtainable with the volumeter assembly such as shown in FIGS. 8A and 8B. The volumetric data of FIG. 9 were obtained with a Coulter Model ZB Coulter Counter and sample stand, which includes a constant current source but which does not contain subsystems providing either fluidic or post-collection compensation for particle coincidence, recirculating particles, or those transiting the conduit near its wall. Two Coulter aperture tubes were used to acquire particle volumetric data, one according to U.S. Pat. No. 2,985,830 and the other a similar tube in which a volumeter assembly according to FIGS. 8A and 8B was substituted for the traditional Coulter wafer. The standard aperture tube comprised a Coulter conduit wafer with a conduit having D=0.100 mm and L/D=0.75. The volumeter assembly consisted of discs of platinum 2.5 mm in outer diameter, one 0.20 mm thick (52 in FIGS. 8A and 8B) and one 0.10 mm thick (53 in FIG. 8B), centered one per side on a ruby disc (W in FIGS. 8A and 8B) 4.0 mm in outer diameter and 0.122 mm in thickness. The platinum discs were attached to the ruby disc with two-part commercial epoxy adhesive according to the manufacturer's instructions. The cured assembly was perforated and finished to form a circular volumeter conduit having a functional Coulter conduit of diameter D'=0.100 mm and L'/D'=1.22, as is known in the art of making Coulter wafers. The completed volumeter assembly was mounted with two-part commercial epoxy adhesive onto a second aperture tube (from which the standard conduit wafer had been removed) so that in use the 0.20 mm platinum collar formed the entry side of conduit C. Volumetric data for latex particles approximately 0.005 mm in diameter, suspended at high concentration in isotonic saline, were obtained using both aperture tubes with identical instrument settings.

The pulse data from the Model ZB Counter was coupled to a Coulter Model C-1000 Channelyzer which uses pulse-height analysis methods to measure particle volume; the Model C-1000 instrumentation contains pulse-edit circuitry which can be disabled, as was done to collect all data in FIG. 9. In this figure, histogram 43' is uncorrected data from the standard Coulter aperture tube; the histogram artifact due to recirculating particles ($D_T$ in FIG. 2) is included in region 41' with electronic noise, while that due to excessive particle coincidence and particle trajectories such as $B_T$ or $C_T$ in FIG. 2 appears as skewness 42'. Histogram 40' is data from the identical dense particle suspension obtained with the identical instrument settings as histogram 43', but with the aperture tube incorporating the volumeter assembly. Volumetric artifacts 41' and 42' in histogram 43' are substantially eliminated in histogram 40'.

It should be noted that the difference in modal particle volumes between histograms 40' and 43' has two components: Firstly, L'/D'=1.22 for 40', compared to L/D=0.75 for 43', and the larger electrical resistance of the liquid in the volumeter conduit reduces the particle contrast for identical particle size and excitation currents; and secondly, due to the field-shaping effects of the conductive collars, the apparent resistance of a given Coulter conduit wafer used in the field-amending conduit is higher than for the same Coulter conduit wafer used conventionally. As is known in the Coulter art, these effects can be electrically calibrated out so that the modal particle volumes of the two histograms coincide; this was not done in FIG. 9 to keep all experimental parameters identical except the volumeter conduit. When volumetric calibration was independently done for the two volumeter tubes, the non-artifactual portion of histogram 43' overlay histogram 40'.

Similar improvement in the quality of volumetric data was also achieved when aperture tubes incorporating other volumeter assemblies according to various embodiments were substituted for the standard Coulter aperture tube in the apparatus described in U.S. Pat. No. 2,656,508 or 3,259,842. This apparatus was commercialized as the Coulter Model A Coulter Counter or the Coulter Model B Coulter Counter, respectively. The Model A Coulter Counter includes a voltage source to supply the excitation current and a single threshold circuit for sizing particles; it was the first commercial instrument based on the Coulter principle. The Model B Coulter Counter includes a current source to supply the excitation current and a dual-threshold circuit for sizing particles. Neither apparatus comprises subsystems providing either fluidic or post-collection compensation for particle coincidence, recirculating particles, or those transiting the conduit near its wall. With aperture tubes including assemblies according to either Embodiments 2 or 4, both a Model A and a Model B Coulter Counter provided near-ideal volumetric histograms (similar to 40' in FIG. 9) when used with a Coulter Model C-1000 Channelyzer in which the coincidence pulse-edit circuitry was disabled. Similar results were obtained when such field-amending volumeter assemblies were tested with contemporary apparatus in which facilitating art had been disabled.

Figure 10:
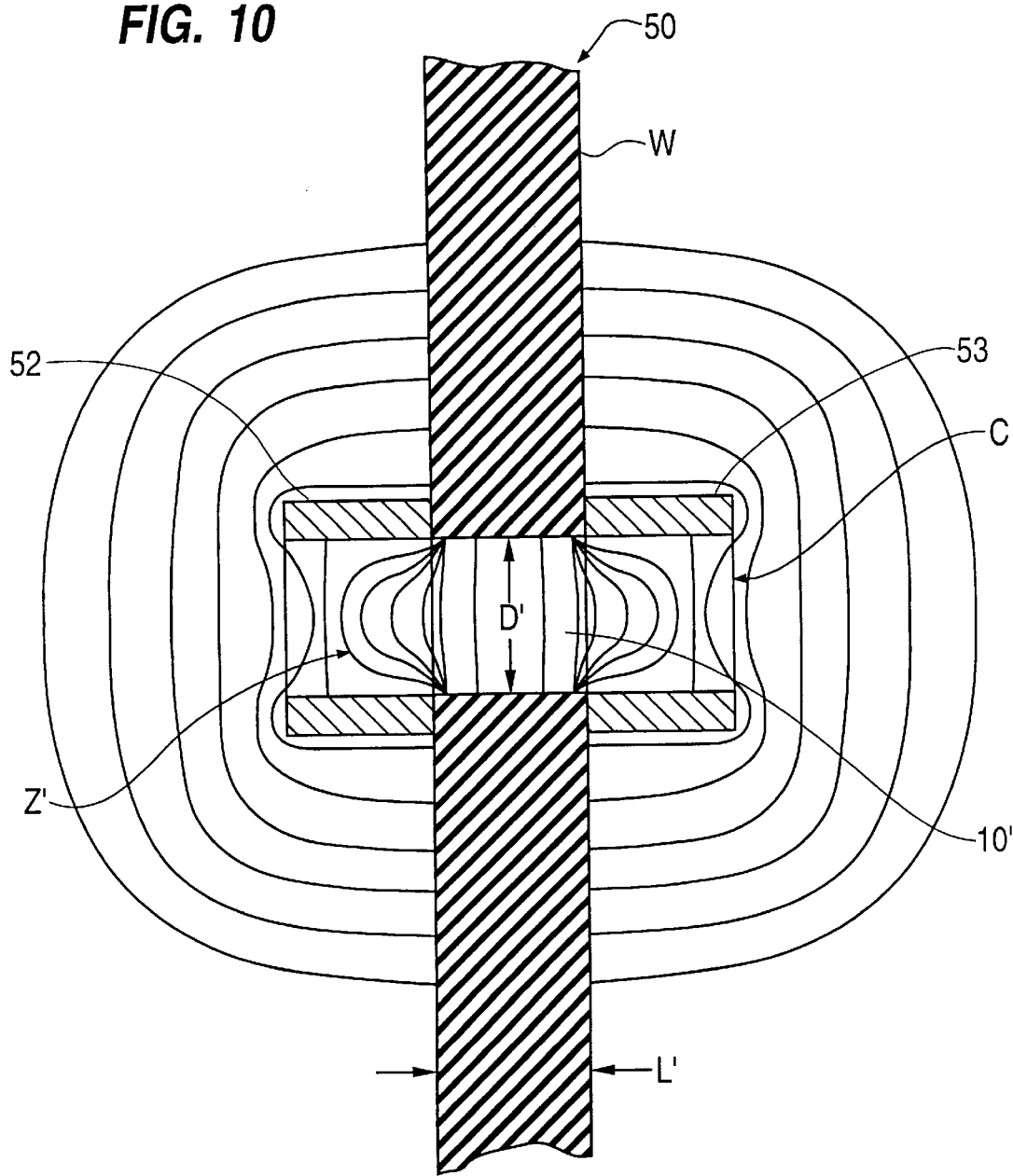
FIGS. 10–13 illustrate longitudinal sections of alternative embodiments of the volumeter assembly of the invention.

In FIG. 10 is illustrated a volumeter assembly 50 similar to that of FIGS. 8A and 8B, except that conductive collars 52 and 53 have outer diameters only slightly larger (e.g., ≅1.5D') than diameter D' of functional conduit 10' in conduit wafer W. Such tubular collars provide the internal particle-sensitive zone Z' and the primary hydrodynamic advantages of the large-diameter elements 52 and 53 in FIGS. 7, 8A, and 8B, but a different distribution of the electric field and less favorable secondary fluidic properties external to field-amending conduit C. Consequently, the outer collar diameters may be selected to provide electrical characteristics not available with traditional Coulter conduits. For example, the outer diameters of collars 52 and 53 may be chosen to control electric field uniformity and current density in the particle-suspending liquid near the entry to conduit C, in which case it is preferred that the outer diameter of the collars should be at least several times greater than the conduit diameter D', as in FIGS. 7, 8A, and 8B. Alternatively, impedances for DC and AC excitation currents may be decoupled, since the former depends only on the physical dimensions of functional conduit 10' and the properties of the particle-suspending liquid M, whereas the latter also depends on the lateral dimensions of collars 52 and 53 and the dielectric properties of the conduit wafer W used to form conduit C. Thus, the DC impedance for volumeter assembly 50 in FIGS. 8A and 8B is not significantly different from that of volumeter assembly 50 in FIG. 10, but the AC impedances of the two volumeter assemblies differ substantially, due to the different cross-sectional area of respective collar-pair 52 and 53 contacting conduit wafer W.

In some applications, volumeter conduits including such disc or tubular collars may benefit from making element 51 from a lossy ceramic as discussed in Embodiment 7, from providing element 52 a shaped inlet as discussed in Embodiment 6, or from coating or plating the conductive preforms for elements 52 and 53 to provide a combination of material properties not available with the base material as discussed in Embodiment 5.

EMBODIMENT 5

Although the above embodiments comprise low-resistivity elements made of homogeneous conductive materials, in general these elements (e.g., 52 or 53 in FIGS.

Figure 11:
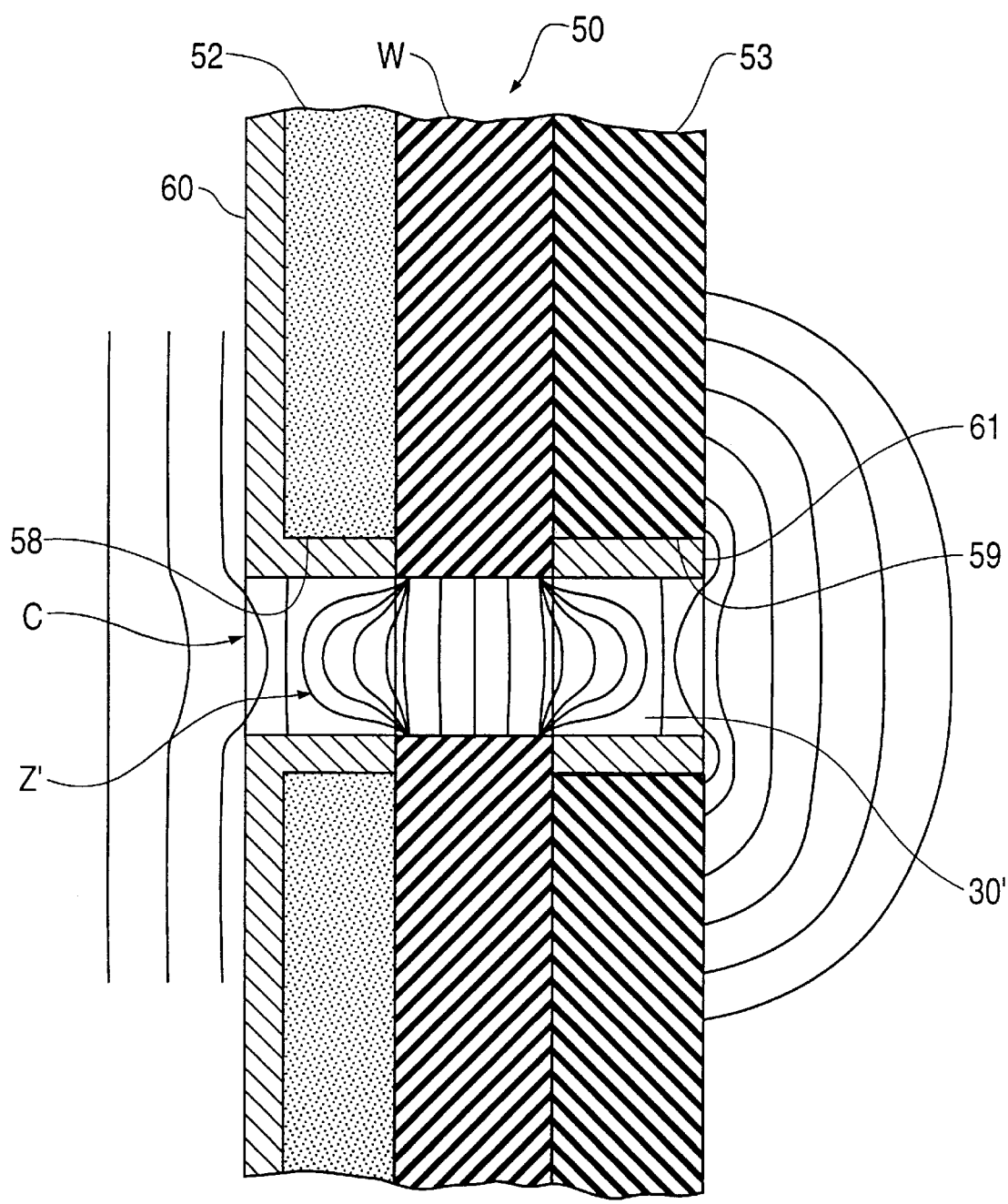

7, 8B, and 10) may be formed from one material and coated or plated with another material in order to provide combinations of material properties unobtainable with the individual materials. In FIG. 11 is illustrated a volumeter assembly 50 which incorporates two such collars 52 and 53 attached to Coulter conduit wafer W so as to form hydrodynamically smooth conduit C. Conductive coating or plating 60 over the outer face and through opening 58 of collar 52 permits it to establish the electric field distribution seen with homogeneous conducting elements 52 or 53 in FIG. 7 or 8B. Conductive coating or plating 61 through opening 59 of dielectric collar 53 permits it to establish the electric field distribution seen with the tubular homogeneous conducting collars 52 or 53 in FIG. 10, but without the unfavorable secondary hydrodynamic properties. Such coatings or platings 60 and 61 preferably produce an effective resistivity in those portions of wall 30' surrounded by elements 52 and 53 which is less than that of the suspending medium M. Some applications may benefit from metalization (e.g., platinization) of elements 52 and 53, while others may benefit from similar use of a conductive oxide (e.g., of tin or indium). The resulting sensitive zone Z' within field-amending conduit C is substantially identical to those in FIGS. 7 and 10, irrespective of the direction of suspension flow through conduit C in FIG. 11 or of whether both collars are identically the form of either collar 52 or 53 in FIG. 11. However, the external electric field distributions in the particle-suspending liquid M between the collar faces and excitation electrodes will depend on the area of conductor exposed to the suspending medium.

The AC impedance of conduit C in FIG. 11 will depend on the electrical properties of the material used to make the collars, particularly so for collars (e.g., collar 52) coated or plated on a lateral surface. In principle, the field characteristics required in the field-amending conduit C may be provided by such collars made of either a dielectric or a conductive material, i.e., either a conductive or an insulative ceramic plated to form metallic coating 60 in order to provide a particular combination of electrical conductivity and chemical stability. However, the AC impedance of volumeter assembly 50 comprising a pair of collars of the form of collar 52 in FIG. 11 will vary significantly, depending on whether such collars are made from a conductive or insulative material. If the collars are made from a dielectric material, then the AC impedance of conduit C will also depend on the dielectric properties of the material unless a conductive material is used to join the collars to conduit wafer W, i.e., brazing or use of a metal-filled adhesive will yield an impedance similar to that given by a homogeneous conductive collar of similar dimensions. In general, such collars may be formed of any material providing the desired combination of electrical and physical properties. Other surfaces of such collars may be selectively coated or plated to provide a selection of electrical characteristics, if at least the wall of collar openings 58 and 59 is made conductive with a suitable coating or plating. The latter structure, in which both collars 52 and 53 are coated or plated only through their respective openings 58 and 59, is the minimal embodiment of the field-amending concept and may in principle be realized by appropriately coating or plating portions of conduit 10' in conduit wafer W having $L'/D' \geq 3$.

In some applications, volumeter conduits resulting from such implementations may benefit from making element 51 from a lossy ceramic as discussed in Embodiment 7 or from providing element 52 a shaped inlet as discussed in Embodiment 6.

EMBODIMENT 6

Figure 12:
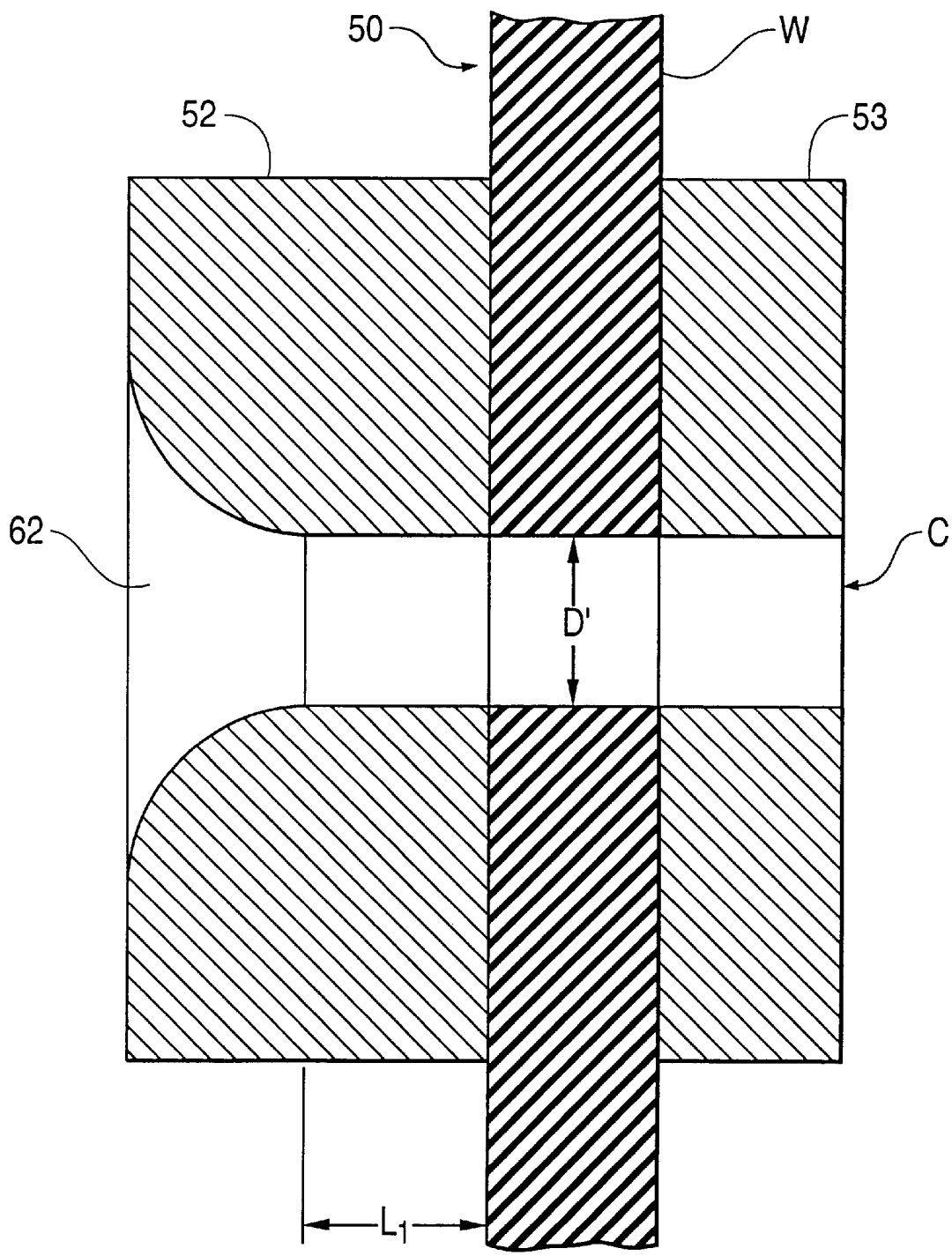

The axial distribution of conduit cross-sections of the collars may be designed to provide desired electric or hydrodynamic distributions in the conduit ambits. For example, the total length $L_1$ of element 52 in FIG. 7, 8B or 11 required to attain a given modal particle trajectory may be shortened without loss of hydrodynamic benefits if a radiussed or trumpet-shaped entry region is provided on its entry edge. Such a shaped entry is known in the art to provide improved flow properties through the conduit (U.S. Pat. No. 3,739,258), but in prior-art volumeter conduits shaped entries degrade pulse characteristics and are difficult to repeatably produce in the usual dielectric materials. However, in the field-amending conduit pulse characteristics may be made independent of the shaped entry, since the particle-sensitive zone is decoupled from the hydrodynamic length of conduit C. Thus, if a straight conduit section of minimum length $L_1$=D' is interposed between conduit wafer W and the shaped entry 62 in conductive element 52 as shown in volumeter assembly 50 of FIG. 12, the hydrodynamic benefits of the shaped entry may be gained without degrading pulse characteristics. Preferably, shaped entry 62 is made to have a longitudinal profile of exponential shape, but it may be given a toroidal form with radius approximately D'/2 or greater. Such shaped entries are comparatively simple to form in many of the conductive materials useful in making elements 52 or 53, and due to averaging in the developing laminar flow, imperfections in such shaped entries 62 are less significant than with shaped entries in prior-art conduits formed in dielectric materials. In some applications, volumeter conduits resulting from such implementations may benefit from making element 51 from a lossy ceramic as discussed in Embodiment 7 or from coating or plating the preforms for elements 52 and 53 to provide a combination of material properties not available with the base material as discussed in Embodiment 5.

EMBODIMENT 7

Although the above embodiments comprise a high-resistivity element (e.g., 51 in FIG. 7 or W in FIGS. 8B, 10, 11, and 12) made of an excellent dielectric material, in general the high-resistivity element in any of the preceding embodiments may be made of a lossy dielectric such as a conductive glass, a conductive ceramic, a type of conductive polymer or plastic, or other such material. The resistivity of such lossy dielectric is preferably substantially greater than that of the particle-suspending medium M but less than that of, e.g., ruby, alumina, or quartz. An appropriate choice of such material may be useful in further shaping the electric field within the functional Coulter conduit, e.g., 10' in the FIG. 7 volumeter assembly 50, to improve field homogeneity. Use of lossy dielectrics in the high-resistivity element may be particularly beneficial in conduits C for which $L' \leq D'$, whereby the poor pulse-amplitude development of such conduits may be improved.

Assembly and joining methods must be compatible with the specific lossy dielectric selected for the high-resistivity element. Benefits of lossy dielectrics may also be provided by depositing a thin metallic layer, e.g., gold or nickel, of controlled resistivity through the conduit of a traditional Coulter conduit wafer and incorporating said wafer as wafer W in e.g., FIG. 8B, 11 or 12.

EMBODIMENT 8

Figure 13:
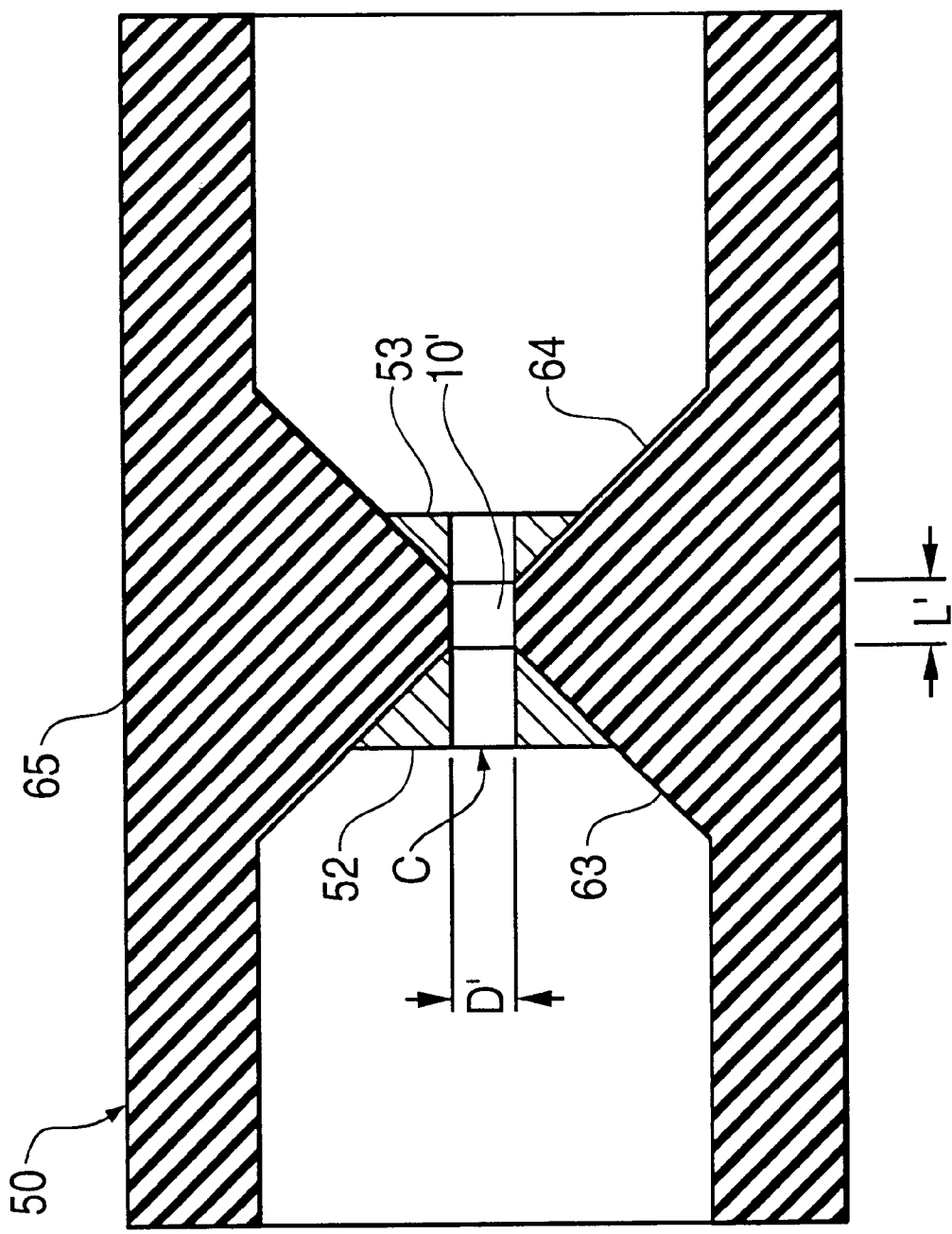

According to the alternative embodiment illustrated in FIG. 13, the volumeter assembly 50 is constructed as a flow cell of the type described in U.S. Pat. No. 3,628,140 or U.S. Pat. No. 4,515,274. Such flow cells are usually made from an optically transparent material such as fused quartz, synthetic silica, sapphire or beryllia and are typically used in apparatus combining the Coulter principle with optical sensing modalities. Such apparatus most commonly includes fluidic subsystems providing hydrodynamically focused flow. Typical volumeter conduits C are of constant circular cross-section, of a diameter D' in the 0.030 mm to 0.200 mm range. Suitable collars 52 and 53 of minimal thickness at least approximating the conduit diameter D' are adapted into conical cups 63 and 64 in the dielectric flow cell 65 as may be consistent with other design considerations. The thicknesses of collars 52 and 53 combine with the length L' of functional conduit 10' to form hydrodynamically smooth conduit C. The distribution of the electric field is substantially similar to that in FIG. 7, with the particle-sensitive zone internal to field-amending conduit C. Collars 52 and 53 may be made of a platinum alloy or other appropriate material; if desired, collars 52 and 53 may also be inset into flow cell 65 so that the outer collar surfaces are smoothly continuous with the conical cups 63 or 64. Joining of elements 52 and 53 to flow cell 65 may be by, e.g., methods normally used to provide electrodes in flow-cell assemblies.

Volumeter assemblies comprising conduits of prismatic cross section, for example as discussed in U.S. Pat. No. 4,348,107, may be similarly provided the additional advantages of the invention by appropriately incorporating collars of minimal thickness at least approximating the diagonal of the particular conduit cross section.

It is obvious that hydrodynamically focused flow may be used with field-amending volumeter conduits, either to stabilize the suspension flow through the conduit or to attain the characteristics of its sensitive zone. If hydrodynamically focused flow is used with, e.g., the field-amending flow cell of FIG. 13, element or collar 53 may not be needed since the sheath flow can be made to substantially prevent extraneous pulses from particles on recirculation trajectories. However, in numerous applications the length $L_1$ and entry shape of element or collar 52 may be selected (as discussed in Embodiment 6) so that acceptable performance can be achieved without use of hydrodynamically focused flow, in which case it is preferred that element or collar 53 be included in volumeter assembly 50.

As will be apparent from the preceding discussion and description of the several embodiments, the field-amending volumeter conduit of this invention differs from known prior-art volumeter conduits in several important distinctions. Firstly, the new volumeter conduit incorporates solid field-amending elements preferably less resistive than the particle-suspending liquid medium adjacent to, and fluidically continuous with, its functional Coulter conduit; thus, prior-art conduit structures having any similarly disposed insulative structure, gap for a liquid electrode in an insulative structure, or liquid-permeated porous medium are all distinguished against on basis of resistivity and consequent function. Secondly, said field-amending elements are indirectly coupled electrically to the excitation electrodes through electrical contact with the suspending liquid and so require no operative connection to external apparatus in order to achieve their primary functions; thus, prior-art conduit structures incorporating similarly located metallic thin electrodes are distinguished against on basis of intended function and independence from accessory apparatus. Thirdly, the axial extents of said field-amending elements are minimally those establishing a desired level of isolation between the external electric fields in the suspending liquid and the internal ambit fields of the conduit sensitive zone; these elements preferably have axial extents at minimum equal to those of the effective ambit electric fields of the functional Coulter conduit, further distinguishing against prior-art conduit structures incorporating similarly located conductive electrodes or elements intentionally made thin in order to minimize their effect on the electric field. Fourthly, in the field-amending conduit the axial extent of the entry field-amending element may be selectively increased above the minimal value to enable development of quasi-laminar flow, thereby permitting independent optimization of the effects of the electric and hydrodynamic fields on particle pulsations and predictable limitation of the number of anomalous particle pulses; such structures are not recognized in the prior conduit art. Therefore, these field-amending elements of lesser resistivity are clearly distinguished from both similarly located insulating structures and electrodes of whatever form in the prior art. It will be obvious to those skilled in the art of particle analysis that the present invention affords many advantages, and offers many design options, not available with the traditional Coulter volumeter conduit. The resulting versatility promises to expand the particle-characterizing art, by enabling cost-effective approaches to particle characterization not practicable with the Coulter conduit.

In the above description, the advance which the invention represents will become apparent to those skilled in this art, and while theories are expressed as an aid to explanation, these are not intended to be limiting, irrespective of their degree of correctness.

What is claimed is:

1. Apparatus for sensing and characterizing particles by the Coulter principle, said apparatus comprising:

(a) a volumeter conduit through which a liquid suspension of particles to be sensed and characterized can be made to pass, said volumeter conduit being hydrodynamically smooth and formed in a solid member having an electrical resistivity which effectively varies along the conduit length to define a conduit having a delimited central region of high electrical resistivity which is smoothly contiguous on its opposing boundaries to uninsulated distal regions of substantially lesser electrical resistivity;

(b) a liquid-handling system for causing said liquid suspension of particles to pass through said volumeter conduit;

(c) a first electrical circuit for producing a nominal electrical excitation current through said volumeter conduit, said excitation current being effective to establish in the vicinity of said volumeter conduit an electric field having a particle-sensitive zone in which changes in said nominal electrical excitation current as produced by particles passing through said volumeter conduit simultaneously with said nominal current are measurable, said uninsulated distal regions independently functioning (i) to shape said electric field so as to substantially confine said particle-sensitive zone within the physical boundaries of said volumeter conduit; (ii) to enable development of quasi-laminar flow through said sensitive zone so as to increase the proportion of particles per second transiting substantially homogeneous areas of the sensitive zone; and (iii) to prevent particles that have already passed through said conduit and are on recirculating trajectories from re-entering said particle-sensitive zone; and (d) a second electrical circuit for monitoring the amplitude of the electrical current through said volumeter conduit to sense the characteristics of particles passing through said conduit.

2. The apparatus as defined by claim 1 wherein said solid member is a three-element structure composed of a layer of material having high electrical resistivity disposed between, and contiguous with, a pair of layers of material of lesser resistivity, and wherein said conduit is formed by through-holes respectively formed in each of said layers, said through-holes being of the same size and shape and being fluidically aligned to form a hydrodynamically continuous and smooth conduit passing through said three-element structure.

3. The apparatus as defined by claim 1 wherein said solid member comprises an intrinsic semiconductor wafer which is suitably doped with an electrically active impurity to provide said delimited central region of high electrical resistivity which is smoothly contiguous on its opposing boundaries to uninsulated distal regions of substantially lesser electrical resistivity.

4. The apparatus as defined by claim 1 wherein said solid member comprises a unitary assembly comprising three complementary and contiguous ceramic elements, the center ceramic element being substantially pure and the outer ceramic elements being either a conductive ceramic or a ceramic infiltrated with a metallic material to enhance the conductivity thereof, and wherein said conduit is formed by through-holes respectively formed in each of said ceramic elements, said through-holes being of the same size and shape and being fluidically aligned to form said hydrodynamically smooth conduit.

5. The apparatus as defined by claim 1 wherein said solid member comprises a unitary assembly comprising three complementary and contiguous elements, the center element being made of a substantially pure ceramic and the outer elements being made of a metallic material, and wherein said conduit is formed by through-holes respectively formed in each of said elements, said through-holes being of the same size and shape and being fluidically aligned to form said hydrodynamically smooth conduit.

6. The apparatus as defined by claim 1 wherein said volumeter assembly comprises a flow cell having a wall of dielectric material which defines said delimited central region of said conduit and a pair of conductive collars which define said distal regions.

7. The apparatus as defined by claim 5 wherein the through-hole formed in one of said outer ceramic elements gradually increases in diameter to provide a trumpet-shaped or radiussed opening through which a particle suspension can readily enter said conduit.

8. The apparatus as defined by claim 1 wherein said volumeter conduit has a circular cross-section.

9. The apparatus as defined by claim 1 wherein said volumeter conduit has a rectangular cross-section.

10. The apparatus as defined by claim 1 wherein said volumeter conduit is defined by (a) a through-hole formed in a wafer of dielectric material, and (b) central openings respectively formed in a pair of electrically-conductive collars, said central openings and said through-hole being of identical size and shape, said collars being disposed on opposite sides of said wafer so that their respective openings and said through-hole collectively form a hydrodynamically smooth conduit.

11. The apparatus as defined by claim 10 wherein said volumeter conduit has a circular cross-section, and wherein each of said collars is circular in shape and has a diameter approximately 1.5 to 10 times the diameter of said volumeter conduit.

12. The apparatus as defined by claim 10 wherein each of said collars has a thickness approximately 1 to 10 times the thickness of said wafer.

13. The apparatus as defined by claim 10 wherein each of said collars comprises a material selected from the group consisting of metals of the platinum group, gold, nickel, tungsten, titanium, alloys of said metals, silicon carbide, titanium carbide, and tungsten carbide.

14. The apparatus as defined by claim 10 wherein at least the central openings of said collars are plated with a metallic material selected from the group consisting of metals of the platinum group, gold, titanium, and alloys of such metals.

15. The apparatus as defined by claim 10 wherein said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

16. The apparatus as defined by claim 10 wherein the material of one collar differs from that of the other collar.

17. The apparatus as defined by claim 10 wherein at least one of said collars constitutes a structural component of said liquid-handling system.

18. The apparatus as defined by claim 10 wherein said collars have substantially the same thickness.

19. The apparatus as defined by claim 10 wherein the thickness of one collar differs from that of the other collar.

20. The apparatus as defined by claim 10 wherein said wafer comprises a material selected from the group consisting of sapphire, ruby, alumina, quartz, glass, beryllia, and lossy dielectrics.

21. Particle -sensing and -characterizing apparatus comprising: (i) a wafer of electrically insulative material having a through-hole therein through which a liquid suspension of particles is adapted to pass, such liquid suspension of particles comprising a particle-suspending medium having an electrical impedance that differs from that of said particles; (ii) a pair of electrically conductive collars, each collar having an opening centrally located therein, said collars being attached to opposite sides of said wafer in positions overlying regions surrounding said through-hole, said through-hole and collar openings being of the same size and shape and being arranged to define a hydrodynamically continuous and smooth conduit for the particle suspension; (iii) a first circuit for causing a nominal electrical current through said conduit, said current being effective to establish an electric field in the vicinity of said conduit; and (iv) a second circuit for monitoring changes in said nominal electrical current as produced by particles passing through a particle-sensitive portion of said electric field, said collars having a thickness by which said particle-sensitive portion is confined within the geometric dimensions of said conduit.

22. The apparatus as defined by claim 21 wherein said through-hole and said collar openings are circular in cross-section.

23. The apparatus as defined by claim 21 wherein said through-hole and said collar openings are rectangular in cross-section.

24. The apparatus as defined by claim 21 wherein each of said collars comprises a disc-shaped member of substantially the same diameter.

25. The apparatus as defined by claim 24 wherein the diameter of each disc-shaped member is approximately 1.5 to 10 times the diameter of said through-hole.

26. The apparatus as defined by claim 21 wherein thickness of each collar is approximately 1 to 10 times the thickness of said wafer.

27. The apparatus as defined by claim 21 wherein said collars comprise a material selected from the group consisting of metals of the platinum group, gold, nickel, tungsten, titanium, alloys of said metals, silicon carbide, titanium carbide, and tungsten carbide.

28. The apparatus as defined by claim 21 wherein said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

29. The apparatus as defined by claim 21 wherein at least the central openings of said collars are plated with a metallic material selected from the group consisting of metals of the platinum group, gold, titanium, and alloys of such metals.

30. The apparatus as defined by claim 21 wherein the material of one collar differs from that of the other collar.

31. The apparatus as defined by claim 21 wherein at least one of said collars constitutes a structural component of a liquid-handling system for causing a liquid suspension of particles to pass through said through-hole.

32. The apparatus as defined by claim 21 wherein said collars have substantially the same thickness.

33. The apparatus as defined by claim 21 wherein the thickness of one collar differs from that of the other collar.

34. The apparatus as defined by claim 21 wherein said dielectric material comprises a material selected from the group consisting of sapphire, ruby, alumina, quartz, glass, beryllia and lossy dielectrics.

35. A particle-sensing volumeter assembly adapted for use in an apparatus which characterizes particles by the Coulter principle, said volumeter assembly comprising a solid member having a wall defining a hydrodynamically smooth conduit through which particles to be characterized can be made to pass simultaneously with the passage of an electrical current through said conduit, said electrical current being effective to produce in the vicinity of said conduit an electric field having a particle-sensitive zone through which the passage of said particles is detectable, said wall having an electrical resistivity which varies in an axisymmetric manner along the conduit length to define a delimited central region of high electrical resistivity contiguous on its opposing boundaries to uninsulated distal regions of substantially lesser electrical resistivity, said uninsulated distal regions having a length measured along the longitudinal axis of said conduit which is sufficient to independently (i) shape said electric field so as to substantially confine said particle-sensitive zone within the physical boundaries of the conduit; (ii) enable development of quasi-laminar flow through said particle-sensitive zone so as to increase the proportion of particles per second transiting substantially homogeneous areas of said particle-sensitive zone; and (iii) prevent particles that have already passed through said conduit and are on recirculating trajectories from re-entering said particle-sensitive zone.

36. The apparatus as defined by claim 35 wherein said solid member is a three-element structure composed of a layer of material having high electrical resistivity disposed between, and contiguous with, a pair of layers of material of lesser resistivity, and wherein said conduit is formed by through-holes respectively formed in each of said layers, said through-holes being of the same size and shape and being fluidically aligned to form a hydrodynamically continuous and smooth conduit passing through said three-element structure.

37. The apparatus as defined by claim 35 wherein said solid member comprises an intrinsic semiconductor wafer which is suitably doped with an electrically active impurity to provide said delimited central region of high electrical resistivity which is smoothly contiguous on its opposing boundaries to uninsulated distal regions of substantially lesser electrical resistivity.

38. The apparatus as defined by claim 35 wherein said solid member comprises a unitary assembly comprising three complementary and contiguous ceramic elements, the center ceramic element being substantially pure and the outer ceramic elements being either a conductive ceramic or a ceramic infiltrated with a metallic material to enhance the conductivity thereof, and wherein said conduit is formed by through-holes respectively formed in each of said ceramic elements, said through-holes being of the same size and shape and being fluidically aligned to form said hydrodynamically smooth conduit.

39. The apparatus as defined by claim 38 wherein the through-hole formed in one of said outer ceramic elements gradually increases in diameter to provide a trumpet-shaped or radiussed opening through which a particle suspension can readily enter said conduit.

40. The apparatus as defined by claim 35 wherein said solid member comprises a unitary assembly comprising three complementary and contiguous elements, the center element being made of a substantially pure ceramic and the outer elements being made of a metallic material, and wherein said conduit is formed by through-holes respectively formed in each of said elements, said through-holes being of the same size and shape and being fluidically aligned to form said hydrodynamically smooth conduit.

41. The apparatus as defined by claim 40 wherein the through-hole formed in one of said outer metallic elements gradually increases in diameter to provide a trumpet-shaped or radiussed opening through which a particle suspension can readily enter said conduit.

42. The apparatus as defined by claim 35 wherein said solid member comprises a flow cell having a wall of dielectric material which defines said delimited central region of said conduit and a pair of electrically conductive collars which define said distal regions.

43. The apparatus as defined by claim 42 wherein the through-hole formed in one of said outer ceramic elements gradually increases in diameter to provide a trumpet-shaped or radiussed opening through which a particle suspension can readily enter said conduit.

44. The apparatus as defined by claim 35 wherein said volumeter conduit has a circular cross-section.

45. The apparatus as defined by claim 35 wherein said volumeter conduit has a rectangular cross-section.

46. The apparatus as defined by claim 35 wherein said volumeter conduit is defined by (a) a through-hole formed in a wafer of dielectric material, and (b) central openings respectively formed in a pair of electrically-conductive collars, said central openings and said through-hole being of identical size and shape, said collars being disposed on opposite sides of said wafer so that their respective openings and said through-hole collectively form a hydrodynamically smooth conduit.

47. The apparatus as defined by claim 46 wherein each of said collars is circular in shape and has a diameter approximately 1.5 to 10 times the diameter of said conduit.

48. The apparatus as defined by claim 46 wherein each of said collars has a thickness approximately 1 to 10 times the thickness of said wafer.

49. The apparatus as defined by claim 46 wherein said collars comprise a material selected from the group consisting of metals of the platinum group, gold, nickel, tungsten, titanium, alloys of said metals, silicon carbide, titanium carbide, and tungsten carbide.

50. The apparatus as defined by claim 46 wherein said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

51. The apparatus as defined by claim 46 wherein at least the central openings of said collars are plated with a metallic material selected from the group consisting of metals of the platinum group, gold, nickel, tungsten, titanium, alloys of such metals.

52. The apparatus as defined by claim 46 wherein the material of one collar differs from that of the other collar.

53. The apparatus as defined by claim 46 wherein at least one of said collars constitutes a structural component of a liquid-handling system for causing a liquid suspension of particles to pass through said through-hole.

54. The apparatus as defined by claim 46 wherein said collars have substantially the same thickness.

55. The apparatus as defined by claim 46 wherein the thickness of one collar differs from that of the other collar.

56. The apparatus as defined by claim 46 wherein the central opening in one collar gradually increases through the thickness of the collar to provide a trumpet-shaped or radiussed opening through which a particle suspension can enter said conduit.

57. The apparatus as defined by claim 46 wherein said wafer comprises a material selected from the group consisting of sapphire, ruby, alumina, quartz, glass, beryllia, and lossy dielectrics.

58. A particle-sensing volumeter assembly adapted for use in an apparatus which characterizes particles by the Coulter principle, said volumeter assembly comprising a solid member having a wall defining a hydrodynamically smooth conduit through which particles to be characterized can be made to pass simultaneously with the passage of an electrical current through said conduit, said electrical current being effective to produce in the vicinity of said conduit an electric field having a particle-sensitive zone through which the passage of said particles is detectable, said wall having an electrical resistivity which varies in an axisymmetric manner along the conduit length to define a delimited first region of high electrical resistivity contiguous on at least one of its opposing boundaries to an uninsulated distal region of substantially lesser electrical resistivity, said uninsulated distal region having a length measured along the longitudinal axis of said conduit which is sufficient to independently (i) shape said electric field so as to substantially confine at least a portion of said particle-sensitive zone within the physical boundaries of the conduit; and (ii) either enable development of quasi-laminar flow through said particle-sensitive zone so as to increase the proportion of particles per second transiting substantially homogeneous areas of said particle-sensitive zone, or prevent particles that have already passed through said conduit and are on recirculating trajectories from re-entering said particle-sensitive zone.

59. The apparatus as defined by claim 58 wherein said conduit is defined by (a) a through-hole formed in a wafer of dielectric material, and (b) a central opening formed in an electrically-conductive collar, said central opening and said through-hole being of identical size and shape, said collar being disposed on said wafer so that its respective opening and said through-hole collectively form a hydrodynamically smooth conduit.

60. The apparatus as defined by claim 59 wherein said collar is circular in shape and has a diameter approximately 1.5 to 10 times the diameter of said conduit.

61. The apparatus as defined by claim 59 wherein said collar has a thickness approximately 1 to 10 times the thickness of said wafer.

62. The apparatus as defined by claim 59 wherein said collar comprises a material selected from the group consisting of metals of the platinum group, gold, nickel, tungsten, titanium, alloys of said metals, silicon carbide, titanium carbide, and tungsten carbide.

63. The apparatus as defined by claim 59 wherein said collars comprise a material selected from the group consisting of sapphire, ruby, alumina, quartz, glass, beryllia, silicon carbide, titanium carbide, and tungsten carbide, and wherein at least the central openings of said collars are plated with a metallic material selected from the group consisting of metals of the platinum group, gold, titanium, and alloys of such metals.

64. The apparatus as defined by claim 59 wherein at least the central opening of said collar is plated with a metallic material selected from the group consisting of metals of the platinum group, gold, nickel, tungsten, titanium, alloys of such metals.

65. A method for sensing and characterizing particles by the Coulter principle, said method comprising:

(a) passing a liquid suspension of particles to be sensed and characterized through a volumeter conduit formed in a solid material having an electrical resistivity which effectively varies along the conduit length to define a conduit having a delimited central region of high electrical resistivity which is smoothly contiguous on its opposing boundaries to uninsulated distal regions of substantially lesser electrical resistivity;

(b) producing a nominal electrical excitation current through said volumeter conduit and an electric field in the vicinity of said conduit, said electric field having a particle-sensitive zone in which changes in said nominal electrical excitation current as produced by particles passing through said volumeter conduit simultaneously with said nominal current are measurable, said uninsulated distal regions independently functioning (i) to shape said electric field so as to substantially confine said sensitive zone within the physical boundaries of the conduit; and (ii) to enable development of quasi-laminar flow through said sensitive zone so as to increase the proportion of particles per second transiting substantially homogeneous areas of the sensitive zone; and (c) monitoring the amplitude of the electrical current through said volumeter conduit to sense the presence and characteristics of particles passing through said conduit.

* * * * *

UNITED STATES PATENT AND TRADEMARK OFFICE
CERTIFICATE OF CORRECTION

PATENT NO. : 6,111,398
DATED : August 29, 2000
INVENTOR(S) : Marshall Donnie Graham It is certified that error appears in the above-identified patent and that said Letters Patent is hereby corrected as shown below:

Column 5, line 19, change "$\xi x/(R \Re e)$" to -- $\xi \propto x/(R \Re e)$ --.

Column 20, line 26, change "K=1.325" to -- K=1.3225 --.

Column 21, line 28, change "$\xi x'/(R' \Re e)$" to -- $\xi \propto x'/(R' \Re e)$ --.

Column 22, line 41, change "B" to -- 4B --.

Column 25, line 52, after "titanium" insert --,--.

Column 28, line 57, change "62" to --52--.

Column 39, line 14, after "titanium," insert --and--.

Column 40, line 29, after "titanium," insert --and--.

Signed and Sealed this

Twenty-ninth Day of May, 2001

*Attest:*

NICHOLAS P. GODICI

*Attesting Officer*    *Acting Director of the United States Patent and Trademark Office*